United States Patent
Chen et al.

(10) Patent No.: US 9,938,510 B2
(45) Date of Patent: Apr. 10, 2018

(54) PHOTOBACTERIUM SP. ALPHA-2-6-SIALYLTRANSFERASE VARIANTS

(71) Applicant: The Regents of the University of California, Oakland, CA (US)

(72) Inventors: Xi Chen, Davis, CA (US); Li Ding, Shannxi (CN)

(73) Assignee: The Regents of the University of California, Oakland, CA (US)

(*) Notice: Subject to any disclaimer, the term of this patent is extended or adjusted under 35 U.S.C. 154(b) by 48 days.

(21) Appl. No.: 14/970,302

(22) Filed: Dec. 15, 2015

(65) Prior Publication Data

US 2016/0177275 A1 Jun. 23, 2016

Related U.S. Application Data

(60) Provisional application No. 62/092,697, filed on Dec. 16, 2014.

(51) Int. Cl.
| | | |
|---|---|---|
| *C12N 9/10* | (2006.01) | |
| *C12N 1/20* | (2006.01) | |
| *C12P 19/18* | (2006.01) | |
| *C12P 21/00* | (2006.01) | |

(52) U.S. Cl.
CPC ............ *C12N 9/1081* (2013.01); *C12P 21/00* (2013.01); *C12Y 204/99* (2013.01)

(58) Field of Classification Search
None
See application file for complete search history.

(56) References Cited

PUBLICATIONS

Ding et al., Carbohydrate Res. 408:127-133, Dec. 23, 2014.*
Kakuta et al., Glycobiology 18:66-73, 2008.*
Schultz et al., Proteins Structure and Function, pp. 521-528, Plenum Press, New York, 1987.*
Okino et al., Acta Crystallogr. Sect. F Struct. Biol. Cryst. Commun. 63:662-664, 2007.*
Sun et el., "N-terminal 112 amino acid residues are not required for the sialyltransferase activity of Photobacterium damsela α 2,6-sialyltransferase," Biotechnol. Lett. Apr. 2008, vol. 30(4), pp. 671-676.
Ding et al., "Efficient chemoenzymatic synthesis of sialyl Tn-antigen and derivatives," Chem. Commun. (Camb), Aug. 14, 2011, vol. 47(30), pp. 8691-8693.

* cited by examiner

*Primary Examiner* — David Steadman
(74) *Attorney, Agent, or Firm* — Kilpatrick Townsend and Stockton LLP

(57) ABSTRACT

The present invention provides *Photobacterium* sp. JH-ISH-224 α2-6-sialyltransferase Psp26ST variants and expression cassettes, vectors, and host cells for expressing the Psp26ST variants. Methods of synthesizing sialylated products are also described.

20 Claims, 5 Drawing Sheets

SEQUENCE LISTING

<160> NUMBER OF SEQ ID NOS: 25

<210> SEQ ID NO 1
<211> LENGTH: 1518
<212> TYPE: DNA
<213> ORGANISM: Artificial Sequence
<220> FEATURE:
<223> OTHER INFORMATION: Synthetic Psp26ST(15-501) A366G

<400> SEQUENCE: 1

```
atgtgtaata atagcgaaga aaatacccag agcatcatta aaaatgatat caacaaaacc      60
atcattgatg aagaatacgt gaacctggaa ccgattaatc agagcaatat tagctttacc     120
aaacatagct gggttcagac ctgtggcacc cagcaactgc tgaccgaaca gaataaagaa     180
agcattagcc tgagcgttgt tgcaccgcgt ctggatgatg atgagaaata ttgctttgat     240
tttaatggcg tgagcaataa aggcgaaaaa tatattacca aagtgaccct gaatgttgtg     300
gcaccgagcc tggaagttta tgttgatcat gcaagcctgc cgaccctgca gcagctgatg     360
gatattatta aaagcgaaga agaaaatccg accgcacagc gttatattgc atggggtcgt     420
attgttccga ccgatgagca gatgaaagaa ctgaatatta ccagctttgc cctgattaat     480
aatcatacac cggcagatct ggttcaggaa attgttaaac aggcccagac caaacatcgt     540
ctgaatgtta aactgagcag caataccgca catagctttg ataatctggt gccgattctg     600
aaagagctga attcctttaa taatgtgacc gtgaccaata ttgatctgta tgacgatggc     660
agcgcagagt acgtgaatct gtataattgg cgtgataccc tgaataaaac cgataatctg     720
aaaattggca agattaccct ggaagatgtg attaatggca ttaatgaaga taccagcaat     780
accggcacca gcagcgttta taattggcag aaactgtatc cggcaaatta tcatttctg     840 cgtaaagact acctgaccct ggaaccgagc tgcatgaact gcgtgatta tattggcgat     900 agcctgaaac aaatgcagtg ggatggcttt aaaaaattta atagcaaaca gcaggaactg     960
tttctgagca ttgtgaattt tgataaacag aaactgcaga tgaatataa tagcagcaat    1020 ctgccgaact ttgttttttac cggcaccacc gtttggggtg gtaatcatga acgtgagtat    1080
tatgccaaac agcagattaa tgtgattaat aatgcgatta tgaaagctc tccgcattat    1140 ctgggtaata gctatgacct gttttttaaa ggtcatccgg tggtggtat tattaatacc    1200 ctgattatgc agaattatcc gagcatggtt gatattccga gcaaaatttc ctttgaagtg    1260
ctgatgatga ccgatatgct gccggatgca gttgcaggta ttgcaagcag cctgtatttt    1320
accattccgg cagaaaaaat caaatttatt gtgtttacca gcaccgaaac cattaccgat    1380
cgtgaaaccg cactgcgttc tccgctggtt caggttatga ttaaactggg cattgtgaag    1440
gaggaaaacg tcctgttttg ggcactcgag caccaccacc accaccactg agatccggct    1500
gctaacaaag cccgaaag                                                   1518
```

<210> SEQ ID NO 2
<211> LENGTH: 487
<212> TYPE: PRT
<213> ORGANISM: Artificial Sequence
<220> FEATURE:
<223> OTHER INFORMATION: Synthetic Psp26ST(15-501) A366G

<400> SEQUENCE: 2

```
Cys Asn Asn Ser Glu Glu Asn Thr Gln Ser Ile Ile Lys Asn Asp Ile
1               5                   10                  15

Asn Lys Thr Ile Ile Asp Glu Glu Tyr Val Asn Leu Glu Pro Ile Asn
            20                  25                  30

Gln Ser Asn Ile Ser Phe Thr Lys His Ser Trp Val Gln Thr Cys Gly
        35                  40                  45

Thr Gln Gln Leu Leu Thr Glu Gln Asn Lys Glu Ser Ile Ser Leu Ser
    50                  55                  60

Val Val Ala Pro Arg Leu Asp Asp Asp Glu Lys Tyr Cys Phe Asp Phe
65                  70                  75                  80

Asn Gly Val Ser Asn Lys Gly Glu Lys Tyr Ile Thr Lys Val Thr Leu
                85                  90                  95
```

-continued

```
Asn Val Val Ala Pro Ser Leu Glu Val Tyr Val Asp His Ala Ser Leu
            100                 105                 110
Pro Thr Leu Gln Gln Leu Met Asp Ile Ile Lys Ser Glu Glu Asn
            115                 120                 125
Pro Thr Ala Gln Arg Tyr Ile Ala Trp Gly Arg Ile Val Pro Thr Asp
            130                 135                 140
Glu Gln Met Lys Glu Leu Asn Ile Thr Ser Phe Ala Leu Ile Asn Asn
145                 150                 155                 160
His Thr Pro Ala Asp Leu Val Gln Glu Ile Val Lys Gln Ala Gln Thr
                165                 170                 175
Lys His Arg Leu Asn Val Lys Leu Ser Ser Asn Thr Ala His Ser Phe
            180                 185                 190
Asp Asn Leu Val Pro Ile Leu Lys Glu Leu Asn Ser Phe Asn Asn Val
            195                 200                 205
Thr Val Thr Asn Ile Asp Leu Tyr Asp Asp Gly Ser Ala Glu Tyr Val
            210                 215                 220
Asn Leu Tyr Asn Trp Arg Asp Thr Leu Asn Lys Thr Asp Asn Leu Lys
225                 230                 235                 240
Ile Gly Lys Asp Tyr Leu Glu Asp Val Ile Asn Gly Ile Asn Glu Asp
                245                 250                 255
Thr Ser Asn Thr Gly Thr Ser Ser Val Tyr Asn Trp Gln Lys Leu Tyr
            260                 265                 270
Pro Ala Asn Tyr His Phe Leu Arg Lys Asp Tyr Leu Thr Leu Glu Pro
            275                 280                 285
Ser Leu His Glu Leu Arg Asp Tyr Ile Gly Asp Ser Leu Lys Gln Met
            290                 295                 300
Gln Trp Asp Gly Phe Lys Lys Phe Asn Ser Lys Gln Gln Glu Leu Phe
305                 310                 315                 320
Leu Ser Ile Val Asn Phe Asp Lys Gln Lys Leu Gln Asn Glu Tyr Asn
                325                 330                 335
Ser Ser Asn Leu Pro Asn Phe Val Phe Thr Gly Thr Thr Val Trp Gly
            340                 345                 350
Gly Asn His Glu Arg Glu Tyr Tyr Ala Lys Gln Gln Ile Asn Val Ile
            355                 360                 365
Asn Asn Ala Ile Asn Glu Ser Ser Pro His Tyr Leu Gly Asn Ser Tyr
            370                 375                 380
Asp Leu Phe Phe Lys Gly His Pro Gly Gly Gly Ile Ile Asn Thr Leu
385                 390                 395                 400
Ile Met Gln Asn Tyr Pro Ser Met Val Asp Ile Pro Ser Lys Ile Ser
                405                 410                 415
Phe Glu Val Leu Met Met Thr Asp Met Leu Pro Asp Ala Val Ala Gly
            420                 425                 430
Ile Ala Ser Ser Leu Tyr Phe Thr Ile Pro Ala Glu Lys Ile Lys Phe
            435                 440                 445
Ile Val Phe Thr Ser Thr Glu Thr Ile Thr Asp Arg Glu Thr Ala Leu
            450                 455                 460
Arg Ser Pro Leu Val Gln Val Met Ile Lys Leu Gly Ile Val Lys Glu
465                 470                 475                 480
Glu Asn Val Leu Phe Trp Ala
                485

<210> SEQ ID NO 3
<211> LENGTH: 1518
```

```
<212> TYPE: DNA
<213> ORGANISM: Artificial Sequence
<220> FEATURE:
<223> OTHER INFORMATION: Synthetic Psp26ST(15-501) W365G

<400> SEQUENCE: 3
atgtgtaata atagcgaaga aaatacccag agcatcatta aaaatgatat caacaaaacc      60
atcattgatg aagaatacgt gaacctggaa ccgattaatc agagcaatat tagctttacc     120
aaacatagct gggttcagac ctgtggcacc agcaactgc tgaccgaaca gaataaagaa      180
agcattagcc tgagcgttgt tgcaccgcgt ctggatgatg atgagaaata ttgctttgat     240
tttaatggcg tgagcaataa aggcgaaaaa tatattacca aagtgaccct gaatgttgtg     300
gcaccgagcc tggaagttta tgttgatcat gcaagcctgc cgaccctgca gcagctgatg     360
gatattatta aaagcgaaga gaaaatccg accgcacagc gttatattgc atggggtcgt      420
attgttccga ccgatgagca gatgaaagaa ctgaatatta ccagctttgc cctgattaat     480
aatcatacac cggcagatct ggttcaggaa attgttaaac aggcccagac caaacatcgt     540
ctgaatgtta aactgagcag caataccgca catagctttg ataatctggt gccgattctg     600
aaagagctga attcctttaa taatgtgacc gtgaccaata ttgatctgta tgacgatggc     660
agcgcagagt acgtgaatct gtataattgg cgtgataccc tgaataaaac cgataatctg     720
aaaattggca agattaccct ggaagatgtg attaatggca ttaatgaaga taccagcaat     780
accggcacca gcagcgttta taattggcag aaactgtatc cggcaaatta tcattttctg     840
cgtaaagact acctgacccct ggaaccgagc ctgcatgaac tgcgtgatta tattggcgat     900
agcctgaaac aaatgcagtg ggatggcttt aaaaaattta tagcaaaca gcaggaactg     960
tttctgagca ttgtgaattt tgataaacag aaactgcaga tgaatataa tagcagcaat    1020
ctgccgaact ttgtttttac cggcaccacc gttggcgcag gtaatcatga acgtgagtat    1080
tatgccaaac agcagattaa tgtgattaat aatgcgatta tgaaagctc tccgcattat    1140
ctgggtaata gctatgacct gttttttaaa ggtcatccgg tggtggtat tattaatacc    1200
ctgattatgc agaattatcc gagcatggtt gatattccga gcaaaatttc ctttgaagtg   1260
ctgatgatga ccgatatgct gccggatgca gttgcaggta ttgcaagcag cctgtatttt   1320
accattccgg cagaaaaaat caaatttatt gtgtttacca gcaccgaaac cattaccgat   1380
cgtgaaaccg cactgcgttc tccgctggtt caggttatga ttaaactggg cattgtgaag   1440
gaggaaaacg tcctgttttg ggcactcgag caccaccacc accaccactg agatccggct   1500
gctaacaaag cccgaaag                                                  1518

<210> SEQ ID NO 4
<211> LENGTH: 487
<212> TYPE: PRT
<213> ORGANISM: Artificial Sequence
<220> FEATURE:
<223> OTHER INFORMATION: Synthetic Psp26ST(15-501) W365G

<400> SEQUENCE: 4

Cys Asn Asn Ser Glu Glu Asn Thr Gln Ser Ile Ile Lys Asn Asp Ile
1               5                   10                  15

Asn Lys Thr Ile Ile Asp Glu Glu Tyr Val Asn Leu Glu Pro Ile Asn
            20                  25                  30

Gln Ser Asn Ile Ser Phe Thr Lys His Ser Trp Val Gln Thr Cys Gly
        35                  40                  45

Thr Gln Gln Leu Leu Thr Glu Gln Asn Lys Glu Ser Ile Ser Leu Ser
```

```
                50                  55                  60
Val Val Ala Pro Arg Leu Asp Asp Glu Lys Tyr Cys Phe Asp Phe
 65                  70                  75                  80

Asn Gly Val Ser Asn Lys Gly Glu Lys Tyr Ile Thr Lys Val Thr Leu
                 85                  90                  95

Asn Val Val Ala Pro Ser Leu Glu Val Tyr Val Asp His Ala Ser Leu
                100                 105                 110

Pro Thr Leu Gln Gln Leu Met Asp Ile Ile Lys Ser Glu Glu Glu Asn
                115                 120                 125

Pro Thr Ala Gln Arg Tyr Ile Ala Trp Gly Arg Ile Val Pro Thr Asp
                130                 135                 140

Glu Gln Met Lys Glu Leu Asn Ile Thr Ser Phe Ala Leu Ile Asn Asn
145                 150                 155                 160

His Thr Pro Ala Asp Leu Val Gln Glu Ile Val Lys Gln Ala Gln Thr
                165                 170                 175

Lys His Arg Leu Asn Val Lys Leu Ser Ser Asn Thr Ala His Ser Phe
                180                 185                 190

Asp Asn Leu Val Pro Ile Leu Lys Glu Leu Asn Ser Phe Asn Asn Val
                195                 200                 205

Thr Val Thr Asn Ile Asp Leu Tyr Asp Asp Gly Ser Ala Glu Tyr Val
                210                 215                 220

Asn Leu Tyr Asn Trp Arg Asp Thr Leu Asn Lys Thr Asp Asn Leu Lys
225                 230                 235                 240

Ile Gly Lys Asp Tyr Leu Glu Asp Val Ile Asn Gly Ile Asn Glu Asp
                245                 250                 255

Thr Ser Asn Thr Gly Thr Ser Ser Val Tyr Asn Trp Gln Lys Leu Tyr
                260                 265                 270

Pro Ala Asn Tyr His Phe Leu Arg Lys Asp Tyr Leu Thr Leu Glu Pro
                275                 280                 285

Ser Leu His Glu Leu Arg Asp Tyr Ile Gly Asp Ser Leu Lys Gln Met
                290                 295                 300

Gln Trp Asp Gly Phe Lys Lys Phe Asn Ser Lys Gln Gln Glu Leu Phe
305                 310                 315                 320

Leu Ser Ile Val Asn Phe Asp Lys Gln Lys Leu Gln Asn Glu Tyr Asn
                325                 330                 335

Ser Ser Asn Leu Pro Asn Phe Val Phe Thr Gly Thr Thr Val Gly Ala
                340                 345                 350

Gly Asn His Glu Arg Glu Tyr Tyr Ala Lys Gln Gln Ile Asn Val Ile
                355                 360                 365

Asn Asn Ala Ile Asn Glu Ser Ser Pro His Tyr Leu Gly Asn Ser Tyr
                370                 375                 380

Asp Leu Phe Phe Lys Gly His Pro Gly Gly Ile Ile Asn Thr Leu
385                 390                 395                 400

Ile Met Gln Asn Tyr Pro Ser Met Val Asp Ile Pro Ser Lys Ile Ser
                405                 410                 415

Phe Glu Val Leu Met Met Thr Asp Met Leu Pro Asp Ala Val Ala Gly
                420                 425                 430

Ile Ala Ser Ser Leu Tyr Phe Thr Ile Pro Ala Glu Lys Ile Lys Phe
                435                 440                 445

Ile Val Phe Thr Ser Thr Glu Thr Ile Thr Asp Arg Glu Thr Ala Leu
                450                 455                 460

Arg Ser Pro Leu Val Gln Val Met Ile Lys Leu Gly Ile Val Lys Glu
465                 470                 475                 480
```

Glu Asn Val Leu Phe Trp Ala
            485

<210> SEQ ID NO 5
<211> LENGTH: 1518
<212> TYPE: DNA
<213> ORGANISM: Artificial Sequence
<220> FEATURE:
<223> OTHER INFORMATION: Synthetic Psp26ST(15-501) W365A

<400> SEQUENCE: 5

```
atgtgtaata atagcgaaga aaatacccag agcatcatta aaaatgatat caacaaaacc      60
atcattgatg aagaatacgt gaacctggaa ccgattaatc agagcaatat tagctttacc     120
aaacatagct gggttcagac ctgtggcacc cagcaactgc tgaccgaaca gaataaagaa     180
agcattagcc tgagcgttgt tgcaccgcgt ctggatgatg atgagaaata ttgctttgat     240
tttaatggcg tgagcaataa aggcgaaaaa tatattacca aagtgaccct gaatgttgtg     300
gcaccgagcc tggaagttta tgttgatcat gcaagcctgc cgaccctgca gcagctgatg     360
gatattatta aagcgaaga agaaaatccg accgcacagc gttatattgc atggggtcgt     420
attgttccga ccgatgagca gatgaaagaa ctgaatatta ccagctttgc cctgattaat     480
aatcatacac cggcagatct ggttcaggaa attgttaaac aggcccagac caaacatcgt     540
ctgaatgtta aactgagcag caataccgca catagctttg ataatctggt gccgattctg     600
aaagagctga attcctttaa taatgtgacc gtgaccaata ttgatctgta tgacgatggc     660
agcgcagagt acgtgaatct gtataattgg cgtgataccc tgaataaaac cgataatctg     720
aaaattggca agattaccct ggaagatgtg attaatggca ttaatgaaga taccagcaat     780
accggcacca gcagcgttta taattggcag aaactgtatc cggcaaatta tcattttctg     840
cgtaaagact acctgaccct ggaaccgagc ctgcatgaac tgcgtgatta tattggcgat     900
agcctgaaac aaatgcagtg ggatggcttt aaaaaattta atagcaaaca gcaggaactg     960
tttctgagca ttgtgaattt tgataaacag aaactgcaga tgaatataaa tagcagcaat    1020
ctgccgaact ttgtttttac cggcaccacc gttgcggcag gtaatcatga acgtgagtat    1080
tatgccaaac agcagattaa tgtgattaat aatgcgatta tgaaagctc tccgcattat    1140
ctgggtaata gctatgacct gttttttaaa ggtcatccgg gtggtggtat tattaatacc    1200
ctgattatgc agaattatcc gagcatggtt gatattccga gcaaaatttc ctttgaagtg    1260
ctgatgatga ccgatatgct gccggatgca gttgcaggta ttgcaagcag cctgtatttt    1320
accattccgg cagaaaaaat caaatttatt gtgtttacca gcaccgaaac cattaccgat    1380
cgtgaaaccg cactgcgttc tccgctggtt caggttatga ttaaactggg cattgtgaag    1440
gaggaaaacg tcctgttttg ggcactcgag caccaccacc accaccactg agatccggct    1500
gctaacaaag cccgaaag                                                   1518
```

<210> SEQ ID NO 6
<211> LENGTH: 487
<212> TYPE: PRT
<213> ORGANISM: Artificial Sequence
<220> FEATURE:
<223> OTHER INFORMATION: Synthetic Psp26ST(15-501) W365A

<400> SEQUENCE: 6

Cys Asn Asn Ser Glu Glu Asn Thr Gln Ser Ile Ile Lys Asn Asp Ile
1               5                   10                  15

```
Asn Lys Thr Ile Ile Asp Glu Glu Tyr Val Asn Leu Glu Pro Ile Asn
             20                  25                  30
Gln Ser Asn Ile Ser Phe Thr Lys His Ser Trp Val Gln Thr Cys Gly
         35                  40                  45
Thr Gln Gln Leu Leu Thr Glu Gln Asn Lys Glu Ser Ile Ser Leu Ser
     50                  55                  60
Val Val Ala Pro Arg Leu Asp Asp Glu Lys Tyr Cys Phe Asp Phe
 65                  70                  75                  80
Asn Gly Val Ser Asn Lys Gly Glu Lys Tyr Ile Thr Lys Val Thr Leu
                 85                  90                  95
Asn Val Val Ala Pro Ser Leu Val Tyr Val Asp His Ala Ser Leu
                100                 105                 110
Pro Thr Leu Gln Gln Leu Met Asp Ile Ile Lys Ser Glu Glu Asn
            115                 120                 125
Pro Thr Ala Gln Arg Tyr Ile Ala Trp Gly Arg Ile Val Pro Thr Asp
        130                 135                 140
Glu Gln Met Lys Glu Leu Asn Ile Thr Ser Phe Ala Leu Ile Asn Asn
145                 150                 155                 160
His Thr Pro Ala Asp Leu Val Gln Glu Ile Val Lys Gln Ala Gln Thr
                165                 170                 175
Lys His Arg Leu Asn Val Lys Leu Ser Ser Asn Thr Ala His Ser Phe
            180                 185                 190
Asp Asn Leu Val Pro Ile Leu Lys Glu Leu Asn Ser Phe Asn Asn Val
        195                 200                 205
Thr Val Thr Asn Ile Asp Leu Tyr Asp Asp Gly Ser Ala Glu Tyr Val
210                 215                 220
Asn Leu Tyr Asn Trp Arg Asp Thr Leu Asn Lys Thr Asp Asn Leu Lys
225                 230                 235                 240
Ile Gly Lys Asp Tyr Leu Glu Asp Val Ile Asn Gly Ile Asn Glu Asp
                245                 250                 255
Thr Ser Asn Thr Gly Thr Ser Ser Val Tyr Asn Trp Gln Lys Leu Tyr
            260                 265                 270
Pro Ala Asn Tyr His Phe Leu Arg Lys Asp Tyr Leu Thr Leu Glu Pro
        275                 280                 285
Ser Leu His Glu Leu Arg Asp Tyr Ile Gly Asp Ser Leu Lys Gln Met
    290                 295                 300
Gln Trp Asp Gly Phe Lys Lys Phe Asn Ser Lys Gln Gln Glu Leu Phe
305                 310                 315                 320
Leu Ser Ile Val Asn Phe Asp Lys Gln Lys Leu Gln Asn Glu Tyr Asn
                325                 330                 335
Ser Ser Asn Leu Pro Asn Phe Val Phe Thr Gly Thr Thr Val Ala Ala
            340                 345                 350
Gly Asn His Glu Arg Glu Tyr Tyr Ala Lys Gln Gln Ile Asn Val Ile
        355                 360                 365
Asn Asn Ala Ile Asn Glu Ser Ser Pro His Tyr Leu Gly Asn Ser Tyr
    370                 375                 380
Asp Leu Phe Phe Lys Gly His Pro Gly Gly Ile Ile Asn Thr Leu
385                 390                 395                 400
Ile Met Gln Asn Tyr Pro Ser Met Val Asp Ile Pro Ser Lys Ile Ser
                405                 410                 415
Phe Glu Val Leu Met Met Thr Asp Met Leu Pro Asp Ala Val Ala Gly
            420                 425                 430
Ile Ala Ser Ser Leu Tyr Phe Thr Ile Pro Ala Glu Lys Ile Lys Phe
```

```
                435                 440                 445
Ile Val Phe Thr Ser Thr Glu Thr Ile Thr Asp Arg Glu Thr Ala Leu
    450                 455                 460

Arg Ser Pro Leu Val Gln Val Met Ile Lys Leu Gly Ile Val Lys Glu
465                 470                 475                 480

Glu Asn Val Leu Phe Trp Ala
            485

<210> SEQ ID NO 7
<211> LENGTH: 1518
<212> TYPE: DNA
<213> ORGANISM: Artificial Sequence
<220> FEATURE:
<223> OTHER INFORMATION: Synthetic Psp26ST(15-501) W365S

<400> SEQUENCE: 7
```

| | | |
|---|---|---|
| atgtgtaata atagcgaaga aaatacccag agcatcatta aaaatgatat caacaaaacc | 60 |
| atcattgatg aagaatacgt gaacctggaa ccgattaatc agagcaatat tagctttacc | 120 |
| aaacatagct gggttcagac ctgtggcacc cagcaactgc tgaccgaaca gaataaagaa | 180 |
| agcattagcc tgagcgttgt tgcaccgcgt ctggatgatg atgagaaata ttgctttgat | 240 |
| tttaatggcg tgagcaataa aggcgaaaaa tatattacca aagtgaccct gaatgttgtg | 300 |
| gcaccgagcc tggaagttta tgttgatcat gcaagcctgc cgaccctgca gcagctgatg | 360 |
| gatattatta aagcgaaga agaaaatccg accgcacagc gttatattgc atggggtcgt | 420 |
| attgttccga ccgatgagca gatgaaagaa ctgaatatta ccagctttgc cctgattaat | 480 |
| aatcatacac cggcagatct ggttcaggaa attgttaaac aggcccagac caaacatcgt | 540 |
| ctgaatgtta aactgagcag caataccgca catagctttg ataatctggt gccgattctg | 600 |
| aaagagctga attcctttaa taatgtgacc gtgaccaata ttgatctgta tgacgatggc | 660 |
| agcgcagagt acgtgaatct gtataattgg cgtgataccc tgaataaaac cgataatctg | 720 |
| aaaattggca agattaccct ggaagatgtg attaatggca ttaatgaaga taccagcaat | 780 |
| accggcacca gcagcgttta taattggcag aaactgtatc cggcaaatta tcattttctg | 840 |
| cgtaaagact acctgaccct ggaaccgagc tgcatgaac tgcgtgatta tattggcgat | 900 |
| agcctgaaac aaatgcagtg ggatggcttt aaaaaattta atagcaaaca gcaggaactg | 960 |
| tttctgagca ttgtgaattt tgataaacag aaactgcaga tgaatataa tagcagcaat | 1020 |
| ctgccgaact tgttttttac cggcaccacc gttagcgcag gtaatcatga acgtgagtat | 1080 |
| tatgccaaac agcagattaa tgtgattaat aatgcgatta tgaaagctc tccgcattat | 1140 |
| ctgggtaata gctatgacct gttttttaaa ggtcatccgg gtggtggtat tattaatacc | 1200 |
| ctgattatgc agaattatcc gagcatggtt gatattccga gcaaaatttc ctttgaagtg | 1260 |
| ctgatgatga ccgatatgct gccggatgca gttgcaggta ttgcaagcag cctgtatttt | 1320 |
| accattccgg cagaaaaaat caaatttatt gtgtttacca gcaccgaaac cattaccgat | 1380 |
| cgtgaaaccg cactgcgttc tccgctggtt caggttatga ttaaactggg cattgtgaag | 1440 |
| gaggaaaacg tcctgttttg ggcactcgag caccaccacc accaccactg agatccggct | 1500 |
| gctaacaaag cccgaaag | 1518 |

<210> SEQ ID NO 8
<211> LENGTH: 487
<212> TYPE: PRT
<213> ORGANISM: Artificial Sequence
<220> FEATURE:

<223> OTHER INFORMATION: Synthetic Psp26ST(15-501) W365S

<400> SEQUENCE: 8

```
Cys Asn Asn Ser Glu Glu Asn Thr Gln Ser Ile Ile Lys Asn Asp Ile
1               5                   10                  15

Asn Lys Thr Ile Ile Asp Glu Glu Tyr Val Asn Leu Glu Pro Ile Asn
            20                  25                  30

Gln Ser Asn Ile Ser Phe Thr Lys His Ser Trp Val Gln Thr Cys Gly
        35                  40                  45

Thr Gln Gln Leu Leu Thr Glu Gln Asn Lys Glu Ser Ile Ser Leu Ser
    50                  55                  60

Val Val Ala Pro Arg Leu Asp Asp Glu Lys Tyr Cys Phe Asp Phe
65                  70                  75                  80

Asn Gly Val Ser Asn Lys Gly Glu Lys Tyr Ile Thr Lys Val Thr Leu
                85                  90                  95

Asn Val Val Ala Pro Ser Leu Glu Val Tyr Val Asp His Ala Ser Leu
            100                 105                 110

Pro Thr Leu Gln Gln Leu Met Asp Ile Ile Lys Ser Glu Glu Asn
        115                 120                 125

Pro Thr Ala Gln Arg Tyr Ile Ala Trp Gly Arg Ile Val Pro Thr Asp
    130                 135                 140

Glu Gln Met Lys Glu Leu Asn Ile Thr Ser Phe Ala Leu Ile Asn Asn
145                 150                 155                 160

His Thr Pro Ala Asp Leu Val Gln Glu Ile Val Lys Gln Ala Gln Thr
                165                 170                 175

Lys His Arg Leu Asn Val Lys Leu Ser Ser Asn Thr Ala His Ser Phe
            180                 185                 190

Asp Asn Leu Val Pro Ile Leu Lys Glu Leu Asn Ser Phe Asn Asn Val
        195                 200                 205

Thr Val Thr Asn Ile Asp Leu Tyr Asp Asp Gly Ser Ala Glu Tyr Val
    210                 215                 220

Asn Leu Tyr Asn Trp Arg Asp Thr Leu Asn Lys Thr Asp Asn Leu Lys
225                 230                 235                 240

Ile Gly Lys Asp Tyr Leu Glu Asp Val Ile Asn Gly Ile Asn Glu Asp
                245                 250                 255

Thr Ser Asn Thr Gly Thr Ser Ser Val Tyr Asn Trp Gln Lys Leu Tyr
            260                 265                 270

Pro Ala Asn Tyr His Phe Leu Arg Lys Asp Tyr Leu Thr Leu Glu Pro
        275                 280                 285

Ser Leu His Glu Leu Arg Asp Tyr Ile Gly Asp Ser Leu Lys Gln Met
    290                 295                 300

Gln Trp Asp Gly Phe Lys Lys Phe Asn Ser Lys Gln Gln Glu Leu Phe
305                 310                 315                 320

Leu Ser Ile Val Asn Phe Asp Lys Gln Lys Leu Gln Asn Glu Tyr Asn
                325                 330                 335

Ser Ser Asn Leu Pro Asn Phe Val Phe Thr Gly Thr Val Ser Ala
            340                 345                 350

Gly Asn His Glu Arg Glu Tyr Tyr Ala Lys Gln Gln Ile Asn Val Ile
        355                 360                 365

Asn Asn Ala Ile Asn Glu Ser Ser Pro His Tyr Leu Gly Asn Ser Tyr
    370                 375                 380

Asp Leu Phe Phe Lys Gly His Pro Gly Gly Ile Ile Asn Thr Leu
385                 390                 395                 400
```

```
Ile Met Gln Asn Tyr Pro Ser Met Val Asp Ile Pro Ser Lys Ile Ser
            405                 410                 415

Phe Glu Val Leu Met Met Thr Asp Met Leu Pro Asp Ala Val Ala Gly
        420                 425                 430

Ile Ala Ser Ser Leu Tyr Phe Thr Ile Pro Ala Glu Lys Ile Lys Phe
            435                 440                 445

Ile Val Phe Thr Ser Thr Glu Thr Ile Thr Asp Arg Glu Thr Ala Leu
    450                 455                 460

Arg Ser Pro Leu Val Gln Val Met Ile Lys Leu Gly Ile Val Lys Glu
465                 470                 475                 480

Glu Asn Val Leu Phe Trp Ala
            485
```

<210> SEQ ID NO 9
<211> LENGTH: 1518
<212> TYPE: DNA
<213> ORGANISM: Artificial Sequence
<220> FEATURE:
<223> OTHER INFORMATION: Synthetic Psp26ST(15-501) R153G

<400> SEQUENCE: 9

| | | |
|---|---|---|
| atgtgtaata tagcgaaga aaatacccag agcatcatta aaaatgatat caacaaaacc | 60 |
| atcattgatg aagaatacgt gaacctggaa ccgattaatc agagcaatat tagctttacc | 120 |
| aaacatagct gggttcagac ctgtggcacc cagcaactgc tgaccgaaca gaataaagaa | 180 |
| agcattagcc tgagcgttgt tgcaccgcgt ctggatgatg atgagaaata ttgctttgat | 240 |
| tttaatggcg tgagcaataa aggcgaaaaa tatattacca aagtgaccct gaatgttgtg | 300 |
| gcaccgagcc tggaagttta tgttgatcat gcaagcctgc cgaccctgca gcagctgatg | 360 |
| gatattatta aagcgaaga gaaaatccg accgcacagc gttatattgc atgggggtggt | 420 |
| attgttccga ccgatgagca tgaaagaa ctgaatatta ccagctttgc cctgattaat | 480 |
| aatcatacac cggcagatct ggttcaggaa attgttaaac aggcccagac caaacatcgt | 540 |
| ctgaatgtta aactgagcag caataccgca catagctttg ataatctggt gccgattctg | 600 |
| aaagagctga attcctttaa taatgtgacc gtgaccaata ttgatctgta tgacgatggc | 660 |
| agcgcagagt acgtgaatct gtataattgg cgtgataccc tgaataaaac cgataatctg | 720 |
| aaaattggca agattaccct ggaagatgtg attaatggca ttaatgaaga taccagcaat | 780 |
| accggcacca gcagcgttta taattggcag aaactgtatc cggcaaatta tcattttctg | 840 |
| cgtaaagact acctgaccct ggaaccgagc ctgcatgaac tgcgtgatta tattggcgat | 900 |
| agcctgaaac aaatgcagtg ggatggcttt aaaaaattta tagcaaaaca gcaggaactg | 960 |
| tttctgagca ttgtgaattt tgataaacag aaactgcaga tgaatataaa tagcagcaat | 1020 |
| ctgccgaact tgttttttac cggcaccacc gtttgggcag gtaatcatga acgtgagtat | 1080 |
| tatgccaaac agcagattaa tgtgattaat aatgcgatta tgaaagctc tccgcattat | 1140 |
| ctgggtaata gctatgacct gttttttaaa ggtcatccgg tggtggtat tattaatacc | 1200 |
| ctgattatgc agaattatcc gagcatggtt gatattccga gcaaatttc ctttgaagtg | 1260 |
| ctgatgatga ccgatatgct gccggatgca gttgcaggta ttgcaagcag cctgtatttt | 1320 |
| accattccgg cagaaaaat caaatttatt gtgtttacca gcaccgaaac cattaccgat | 1380 |
| cgtgaaaccg cactgcgttc tccgctggtt caggttatga ttaaactggg cattgtgaag | 1440 |
| gaggaaaacg tcctgtttg ggcactcgag caccaccacc accaccactg agatccggct | 1500 |
| gctaacaaag cccgaaag | 1518 |

<210> SEQ ID NO 10
<211> LENGTH: 487
<212> TYPE: PRT
<213> ORGANISM: Artificial Sequence
<220> FEATURE:
<223> OTHER INFORMATION: Synthetic Psp26ST(15-501) R153G

<400> SEQUENCE: 10

```
Cys Asn Asn Ser Glu Glu Asn Thr Gln Ser Ile Ile Lys Asn Asp Ile
1               5                   10                  15

Asn Lys Thr Ile Ile Asp Glu Glu Tyr Val Asn Leu Glu Pro Ile Asn
            20                  25                  30

Gln Ser Asn Ile Ser Phe Thr Lys His Ser Trp Val Gln Thr Cys Gly
        35                  40                  45

Thr Gln Gln Leu Leu Thr Glu Gln Asn Lys Glu Ser Ile Ser Leu Ser
    50                  55                  60

Val Val Ala Pro Arg Leu Asp Asp Glu Lys Tyr Cys Phe Asp Phe
65                  70                  75                  80

Asn Gly Val Ser Asn Lys Gly Glu Lys Tyr Ile Thr Lys Val Thr Leu
                85                  90                  95

Asn Val Val Ala Pro Ser Leu Glu Val Tyr Val Asp His Ala Ser Leu
            100                 105                 110

Pro Thr Leu Gln Gln Leu Met Asp Ile Ile Lys Ser Glu Glu Glu Asn
        115                 120                 125

Pro Thr Ala Gln Arg Tyr Ile Ala Trp Gly Gly Ile Val Pro Thr Asp
    130                 135                 140

Glu Gln Met Lys Glu Leu Asn Ile Thr Ser Phe Ala Leu Ile Asn Asn
145                 150                 155                 160

His Thr Pro Ala Asp Leu Val Gln Glu Ile Val Lys Gln Ala Gln Thr
                165                 170                 175

Lys His Arg Leu Asn Val Lys Leu Ser Ser Asn Thr Ala His Ser Phe
            180                 185                 190

Asp Asn Leu Val Pro Ile Leu Lys Glu Leu Asn Ser Phe Asn Asn Val
        195                 200                 205

Thr Val Thr Asn Ile Asp Leu Tyr Asp Asp Gly Ser Ala Glu Tyr Val
    210                 215                 220

Asn Leu Tyr Asn Trp Arg Asp Thr Leu Asn Lys Thr Asp Asn Leu Lys
225                 230                 235                 240

Ile Gly Lys Asp Tyr Leu Glu Asp Val Ile Asn Gly Ile Asn Glu Asp
                245                 250                 255

Thr Ser Asn Thr Gly Thr Ser Ser Val Tyr Asn Trp Gln Lys Leu Tyr
            260                 265                 270

Pro Ala Asn Tyr His Phe Leu Arg Lys Asp Tyr Leu Thr Leu Glu Pro
        275                 280                 285

Ser Leu His Glu Leu Arg Asp Tyr Ile Gly Asp Ser Leu Lys Gln Met
    290                 295                 300

Gln Trp Asp Gly Phe Lys Lys Phe Asn Ser Lys Gln Glu Leu Phe
305                 310                 315                 320

Leu Ser Ile Val Asn Phe Asp Lys Gln Lys Leu Gln Asn Glu Tyr Asn
                325                 330                 335

Ser Ser Asn Leu Pro Asn Phe Val Phe Thr Gly Thr Thr Val Trp Ala
            340                 345                 350

Gly Asn His Glu Arg Glu Tyr Tyr Ala Lys Gln Gln Ile Asn Val Ile
        355                 360                 365
```

```
Asn Asn Ala Ile Asn Glu Ser Ser Pro His Tyr Leu Gly Asn Ser Tyr
    370                 375                 380

Asp Leu Phe Phe Lys Gly His Pro Gly Gly Gly Ile Ile Asn Thr Leu
385                 390                 395                 400

Ile Met Gln Asn Tyr Pro Ser Met Val Asp Ile Pro Ser Lys Ile Ser
                405                 410                 415

Phe Glu Val Leu Met Met Thr Asp Met Leu Pro Asp Ala Val Ala Gly
                420                 425                 430

Ile Ala Ser Ser Leu Tyr Phe Thr Ile Pro Ala Glu Lys Ile Lys Phe
            435                 440                 445

Ile Val Phe Thr Ser Thr Glu Thr Ile Thr Asp Arg Glu Thr Ala Leu
    450                 455                 460

Arg Ser Pro Leu Val Gln Val Met Ile Lys Leu Gly Ile Val Lys Glu
465                 470                 475                 480

Glu Asn Val Leu Phe Trp Ala
            485
```

```
<210> SEQ ID NO 11
<211> LENGTH: 1518
<212> TYPE: DNA
<213> ORGANISM: Artificial Sequence
<220> FEATURE:
<223> OTHER INFORMATION: Synthetic Psp26ST(15-501) A124D

<400> SEQUENCE: 11
atgtgtaata atagcgaaga aaatacccag agcatcatta aaaatgatat caacaaaacc      60
atcattgatg aagaatacgt gaacctggaa ccgattaatc agagcaatat tagctttacc     120
aaacatagct gggttcagac ctgtggcacc cagcaactgc tgaccgaaca gaataaagaa     180
agcattagcc tgagcgttgt tgcaccgcgt ctggatgatg atgagaaata ttgctttgat     240
tttaatggcg tgagcaataa aggcgaaaaa tatattacca agtgaccct gaatgttgtg      300 gcaccgagcc tggaagttta tgttgatcat gatagcctgc cgaccctgca gcagctgatg     360
gatattatta aaagcgaaga gaaaatccg accgcacagc gttatattgc atggggtcgt      420
attgttccga ccgatgagca gatgaaagaa ctgaatatta ccagctttgc cctgattaat     480
aatcatacac cggcagatct ggttcaggaa attgttaaac aggcccagac caaacatcgt     540
ctgaatgtta aactgagcag caataccgca catagctttg ataatctggt gccgattctg     600
aaagagctga attcctttaa taatgtgacc gtgaccaata ttgatctgta tgacgatggc     660
agcgcagagt acgtgaatct gtataattgg cgtgataccc tgaataaaac cgataatctg     720
aaaattggca agattaccct ggaagatgtg attaatggca ttaatgaaga taccagcaat     780
accggcacca gcagcgttta taattggcag aaactgtatc cggcaaatta tcattttctg     840
cgtaaagact acctgacccc tggaaccgagc ctgcatgaac tgcgtgatta tattggcgat     900
agcctgaaac aaatgcagtg ggatggcttt aaaaaattta tagcaaaca gcaggaactg     960 tttctgagca ttgtgaattt tgataaacag aaactgcaga tgaatataa tagcagcaat    1020 ctgccgaact tgttttttac cggcaccacc gtttgggcag gtaatcatga acgtgagtat   1080
tatgccaaac agcagattaa tgtgattaat aatgcgatta tgaaagctc tccgcattat    1140 ctgggtaata gctatgacct gtttttttaaa ggtcatccgg gtggtggtat tattaatacc   1200
ctgattatgc agaattatcc gagcatggtt gatattccga gcaaaatttc ctttgaagtg   1260
ctgatgatga ccgatatgct gccggatgca gttgcaggta ttgcaagcag cctgtatttt   1320
```

-continued

```
accattccgg cagaaaaaat caaatttatt gtgtttacca gcaccgaaac cattaccgat    1380
cgtgaaaccg cactgcgttc tccgctggtt caggttatga ttaaactggg cattgtgaag    1440
gaggaaaacg tcctgttttg ggcactcgag caccaccacc accaccactg agatccggct    1500
gctaacaaag cccgaaag                                                  1518
```

<210> SEQ ID NO 12
<211> LENGTH: 487
<212> TYPE: PRT
<213> ORGANISM: Artificial Sequence
<220> FEATURE:
<223> OTHER INFORMATION: Synthetic Psp26ST(15-501) A124D

<400> SEQUENCE: 12

```
Cys Asn Asn Ser Glu Glu Asn Thr Gln Ser Ile Ile Lys Asn Asp Ile
1               5                   10                  15

Asn Lys Thr Ile Ile Asp Glu Glu Tyr Val Asn Leu Glu Pro Ile Asn
            20                  25                  30

Gln Ser Asn Ile Ser Phe Thr Lys His Ser Trp Val Gln Thr Cys Gly
        35                  40                  45

Thr Gln Gln Leu Leu Thr Glu Gln Asn Lys Glu Ser Ile Ser Leu Ser
    50                  55                  60

Val Val Ala Pro Arg Leu Asp Asp Glu Lys Tyr Cys Phe Asp Phe
65                  70                  75                  80

Asn Gly Val Ser Asn Lys Gly Glu Lys Tyr Ile Thr Lys Val Thr Leu
                85                  90                  95

Asn Val Val Ala Pro Ser Leu Glu Val Tyr Val Asp His Asp Ser Leu
            100                 105                 110

Pro Thr Leu Gln Gln Leu Met Asp Ile Ile Lys Ser Glu Glu Glu Asn
        115                 120                 125

Pro Thr Ala Gln Arg Tyr Ile Ala Trp Gly Arg Ile Val Pro Thr Asp
    130                 135                 140

Glu Gln Met Lys Glu Leu Asn Ile Thr Ser Phe Ala Leu Ile Asn Asn
145                 150                 155                 160

His Thr Pro Ala Asp Leu Val Gln Glu Ile Val Lys Gln Ala Gln Thr
                165                 170                 175

Lys His Arg Leu Asn Val Lys Leu Ser Ser Asn Thr Ala His Ser Phe
            180                 185                 190

Asp Asn Leu Val Pro Ile Leu Lys Glu Leu Asn Ser Phe Asn Asn Val
        195                 200                 205

Thr Val Thr Asn Ile Asp Leu Tyr Asp Asp Gly Ser Ala Glu Tyr Val
    210                 215                 220

Asn Leu Tyr Asn Trp Arg Asp Thr Leu Asn Lys Thr Asp Asn Leu Lys
225                 230                 235                 240

Ile Gly Lys Asp Tyr Leu Glu Asp Val Ile Asn Gly Ile Asn Glu Asp
                245                 250                 255

Thr Ser Asn Thr Gly Thr Ser Ser Val Tyr Asn Trp Gln Lys Leu Tyr
            260                 265                 270

Pro Ala Asn Tyr His Phe Leu Arg Lys Asp Tyr Leu Thr Leu Glu Pro
        275                 280                 285

Ser Leu His Glu Leu Arg Asp Tyr Ile Gly Asp Ser Leu Lys Gln Met
    290                 295                 300

Gln Trp Asp Gly Phe Lys Lys Phe Asn Ser Lys Gln Gln Glu Leu Phe
305                 310                 315                 320

Leu Ser Ile Val Asn Phe Asp Lys Gln Lys Leu Gln Asn Glu Tyr Asn
```

```
                325                 330                 335
Ser Ser Asn Leu Pro Asn Phe Val Phe Thr Gly Thr Thr Val Trp Ala
            340                 345                 350

Gly Asn His Glu Arg Glu Tyr Tyr Ala Lys Gln Gln Ile Asn Val Ile
            355                 360                 365

Asn Asn Ala Ile Asn Glu Ser Ser Pro His Tyr Leu Gly Asn Ser Tyr
    370                 375                 380

Asp Leu Phe Phe Lys Gly His Pro Gly Gly Ile Ile Asn Thr Leu
385                 390                 395                 400

Ile Met Gln Asn Tyr Pro Ser Met Val Asp Ile Pro Ser Lys Ile Ser
                405                 410                 415

Phe Glu Val Leu Met Met Thr Asp Met Leu Pro Asp Ala Val Ala Gly
                420                 425                 430

Ile Ala Ser Ser Leu Tyr Phe Thr Ile Pro Ala Glu Lys Ile Lys Phe
            435                 440                 445

Ile Val Phe Thr Ser Thr Glu Thr Ile Thr Asp Arg Glu Thr Ala Leu
        450                 455                 460

Arg Ser Pro Leu Val Gln Val Met Ile Lys Leu Gly Ile Val Lys Glu
465                 470                 475                 480

Glu Asn Val Leu Phe Trp Ala
            485
```

<210> SEQ ID NO 13
<211> LENGTH: 1518
<212> TYPE: DNA
<213> ORGANISM: Artificial Sequence
<220> FEATURE:
<223> OTHER INFORMATION: Synthetic Psp26ST(15-501) A235D

<400> SEQUENCE: 13

```
atgtgtaata atagcgaaga aaatacccag agcatcatta aaaatgatat caacaaaacc      60
atcattgatg aagaatacgt gaacctggaa ccgattaatc agagcaatat tagctttacc     120
aaacatagct gggttcagac ctgtggcacc cagcaactgc tgaccgaaca gaataaagaa     180
agcattagcc tgagcgttgt tgcaccgcgt ctggatgatg atgagaaata ttgctttgat     240
tttaatggcg tgagcaataa aggcgaaaaa tatattacca aagtgaccct gaatgttgtg     300
gcaccgagcc tggaagttta tgttgatcat gcaagcctgc cgaccctgca gcagctgatg     360
gatattatta aaagcgaaga gaaaatccg accgcacagc gttatattgc atggggtcgt     420
attgttccga ccgatgagca gatgaaagaa ctgaatatta ccagctttgc cctgattaat     480
aatcatacac cggcagatct ggttcaggaa attgttaaac aggcccagac caaacatcgt     540
ctgaatgtta aactgagcag caataccgca catagctttg ataatctggt gccgattctg     600
aaagagctga attcctttaa taatgtgacc gtgaccaata ttgatctgta tgacgatggc     660
agcgatgagt acgtgaatct gtataattgg cgtgatacc tgaataaaac cgataatctg     720
aaaattggca agattaccct ggaagatgtg attaatggca ttaatgaaga taccagcaat     780
accggcacca gcagcgttta taattggcag aaactgtatc cggcaaatta tcattttctg     840
cgtaaagact acctgacccct ggaaccgagc ctgcatgaac tgcgtgatta tattggcgat     900
agcctgaaac aaatgcagtg ggatggcttt aaaaaattta tagcaaaaca gcaggaactg     960
tttctgagca ttgtgaattt tgataaacag aaactgcaga tgaatataa tagcagcaat    1020
ctgccgaact tgttttttac cggcaccacc gtttgggcag gtaatcatga acgtgagtat    1080
tatgccaaac agcagattaa tgtgattaat aatgcgatta tgaaagctc tccgcattat    1140
```

```
ctgggtaata gctatgacct gttttttaaa ggtcatccgg gtggtggtat tattaatacc    1200
ctgattatgc agaattatcc gagcatggtt gatattccga gcaaaatttc ctttgaagtg    1260
ctgatgatga ccgatatgct gccggatgca gttgcaggta ttgcaagcag cctgtatttt    1320
accattccgg cagaaaaaat caaatttatt gtgtttacca gcaccgaaac cattaccgat    1380
cgtgaaaccg cactgcgttc tccgctggtt caggttatga ttaaactggg cattgtgaag    1440
gaggaaaacg tcctgttttg ggcactcgag caccaccacc accaccactg agatccggct    1500
gctaacaaag cccgaaag                                                  1518
```

<210> SEQ ID NO 14
<211> LENGTH: 487
<212> TYPE: PRT
<213> ORGANISM: Artificial Sequence
<220> FEATURE:
<223> OTHER INFORMATION: Synthetic Psp26ST(15-501) A235D

<400> SEQUENCE: 14

```
Cys Asn Asn Ser Glu Glu Asn Thr Gln Ser Ile Ile Lys Asn Asp Ile
1               5                   10                  15

Asn Lys Thr Ile Ile Asp Glu Glu Tyr Val Asn Leu Glu Pro Ile Asn
            20                  25                  30

Gln Ser Asn Ile Ser Phe Thr Lys His Ser Trp Val Gln Thr Cys Gly
        35                  40                  45

Thr Gln Gln Leu Leu Thr Glu Gln Asn Lys Glu Ser Ile Ser Leu Ser
    50                  55                  60

Val Val Ala Pro Arg Leu Asp Asp Glu Lys Tyr Cys Phe Asp Phe
65                  70                  75                  80

Asn Gly Val Ser Asn Lys Gly Glu Lys Tyr Ile Thr Lys Val Thr Leu
                85                  90                  95

Asn Val Val Ala Pro Ser Leu Glu Val Tyr Val Asp His Ala Ser Leu
            100                 105                 110

Pro Thr Leu Gln Gln Leu Met Asp Ile Ile Lys Ser Glu Glu Asn
        115                 120                 125

Pro Thr Ala Gln Arg Tyr Ile Ala Trp Gly Arg Ile Val Pro Thr Asp
    130                 135                 140

Glu Gln Met Lys Glu Leu Asn Ile Thr Ser Phe Ala Leu Ile Asn Asn
145                 150                 155                 160

His Thr Pro Ala Asp Leu Val Gln Glu Ile Val Lys Gln Ala Gln Thr
                165                 170                 175

Lys His Arg Leu Asn Val Lys Leu Ser Ser Asn Thr Ala His Ser Phe
            180                 185                 190

Asp Asn Leu Val Pro Ile Leu Lys Glu Leu Asn Ser Phe Asn Asn Val
        195                 200                 205

Thr Val Thr Asn Ile Asp Leu Tyr Asp Asp Gly Ser Asp Glu Tyr Val
    210                 215                 220

Asn Leu Tyr Asn Trp Arg Asp Thr Leu Asn Thr Asp Asn Leu Lys
225                 230                 235                 240

Ile Gly Lys Asp Tyr Leu Glu Asp Val Ile Asn Gly Ile Asn Glu Asp
                245                 250                 255

Thr Ser Asn Thr Gly Thr Ser Ser Val Tyr Asn Trp Gln Lys Leu Tyr
            260                 265                 270

Pro Ala Asn Tyr His Phe Leu Arg Lys Asp Tyr Leu Thr Leu Glu Pro
        275                 280                 285
```

```
Ser Leu His Glu Leu Arg Asp Tyr Ile Gly Asp Ser Leu Lys Gln Met
    290                 295                 300

Gln Trp Asp Gly Phe Lys Lys Phe Asn Ser Lys Gln Gln Glu Leu Phe
305                 310                 315                 320

Leu Ser Ile Val Asn Phe Asp Lys Gln Lys Leu Gln Asn Glu Tyr Asn
                325                 330                 335

Ser Ser Asn Leu Pro Asn Phe Val Phe Thr Gly Thr Thr Val Trp Ala
                340                 345                 350

Gly Asn His Glu Arg Glu Tyr Tyr Ala Lys Gln Gln Ile Asn Val Ile
            355                 360                 365

Asn Asn Ala Ile Asn Glu Ser Ser Pro His Tyr Leu Gly Asn Ser Tyr
370                 375                 380

Asp Leu Phe Phe Lys Gly His Pro Gly Gly Ile Ile Asn Thr Leu
385                 390                 395                 400

Ile Met Gln Asn Tyr Pro Ser Met Val Asp Ile Pro Ser Lys Ile Ser
                405                 410                 415

Phe Glu Val Leu Met Met Thr Asp Met Leu Pro Asp Ala Val Ala Gly
                420                 425                 430

Ile Ala Ser Ser Leu Tyr Phe Thr Ile Pro Ala Glu Lys Ile Lys Phe
            435                 440                 445

Ile Val Phe Thr Ser Thr Glu Thr Ile Thr Asp Arg Glu Thr Ala Leu
450                 455                 460

Arg Ser Pro Leu Val Gln Val Met Ile Lys Leu Gly Ile Val Lys Glu
465                 470                 475                 480

Glu Asn Val Leu Phe Trp Ala
                485
```

<210> SEQ ID NO 15
<211> LENGTH: 32
<212> TYPE: DNA
<213> ORGANISM: Artificial Sequence
<220> FEATURE:
<223> OTHER INFORMATION: Synthetic Synthetic primer A366G

<400> SEQUENCE: 15
ggcaccaccg tttggggtgg taatcatgaa cg         32

<210> SEQ ID NO 16
<211> LENGTH: 37
<212> TYPE: DNA
<213> ORGANISM: Artificial Sequence
<220> FEATURE:
<223> OTHER INFORMATION: Synthetic Synthetic primer W365G

<400> SEQUENCE: 16
ttaccggcac caccgttggc gcaggtaatc atgaacg         37

<210> SEQ ID NO 17
<211> LENGTH: 37
<212> TYPE: DNA
<213> ORGANISM: Artificial Sequence
<220> FEATURE:
<223> OTHER INFORMATION: Synthetic Synthetic primer W365A

<400> SEQUENCE: 17
ttaccggcac caccgttgcg gcaggtaatc atgaacg         37

<210> SEQ ID NO 18
<211> LENGTH: 37
<212> TYPE: DNA

```
<213> ORGANISM: Artificial Sequence
<220> FEATURE:
<223> OTHER INFORMATION: Synthetic Synthetic primer W365S

<400> SEQUENCE: 18
ttaccggcac caccgttagc gcaggtaatc atgaacg                              37

<210> SEQ ID NO 19
<211> LENGTH: 39
<212> TYPE: DNA
<213> ORGANISM: Artificial Sequence
<220> FEATURE:
<223> OTHER INFORMATION: Synthetic Synthetic primer R153G

<400> SEQUENCE: 19
cgttatattg catggggtgg tattgttccg accgatgag                            39

<210> SEQ ID NO 20
<211> LENGTH: 39
<212> TYPE: DNA
<213> ORGANISM: Artificial Sequence
<220> FEATURE:
<223> OTHER INFORMATION: Synthetic primer A124D

<400> SEQUENCE: 20
gaagtttatg ttgatcatga tagcctgccg accctgcag                            39

<210> SEQ ID NO 21
<211> LENGTH: 43
<212> TYPE: DNA
<213> ORGANISM: Artificial Sequence
<220> FEATURE:
<223> OTHER INFORMATION: Synthetic primer A235D

<400> SEQUENCE: 21
tctgtatgac gatggcagcg atgagtacgt gaatctgtat aat                       43

<210> SEQ ID NO 22
<211> LENGTH: 1518
<212> TYPE: DNA
<213> ORGANISM: Artificial Sequence
<220> FEATURE:
<223> OTHER INFORMATION: Synthetic Psp26ST(15-501) WILD TYPE

<400> SEQUENCE: 22
atgtgtaata atagcgaaga aaatacccag agcatcatta aaaatgatat caacaaaacc      60
atcattgatg aagaatacgt gaacctggaa ccgattaatc agagcaatat tagctttacc     120
aaacatagct gggttcagac tgtggcacc cagcaactgc tgaccgaaca gaataaagaa     180
agcattagcc tgagcgttgt tgcaccgcgt ctggatgatg atgagaaata ttgctttgat    240
tttaatggcg tgagcaataa aggcgaaaaa tatattacca aagtgaccct gaatgttgtg    300
gcaccgagcc tggaagttta tgttgatcat gcaagcctgc cgaccctgca gcagctgatg    360
gatattatta aaagcgaaga agaaaatccg accgcacagc gttatattgc atggggtcgt    420
attgttccga ccgatgagca gatgaaagaa ctgaatatta ccagctttgc cctgattaat    480
aatcatacac cggcagatct ggttcaggaa attgttaaac aggcccagac caaacatcgt    540
ctgaatgtta aactgagcag caataccgca catagctttg ataatctggt gccgattctg    600
aaagagctga attccttaa taatgtgacc gtgaccaata ttgatctgta tgacgatggc    660
agcgcagagt acgtgaatct gtataattgg cgtgataccc tgaataaaac cgataatctg    720
aaaattggca agattacct ggaagatgtg attaatggca ttaatgaaga taccagcaat    780
```

```
accggcacca gcagcgttta taattggcag aaactgtatc cggcaaatta tcattttctg    840
cgtaaagact acctgaccct ggaaccgagc ctgcatgaac tgcgtgatta tattggcgat    900
agcctgaaac aaatgcagtg ggatggcttt aaaaaattta atagcaaaca gcaggaactg    960
tttctgagca ttgtgaattt tgataaacag aaactgcaga atgaatataa tagcagcaat   1020
ctgccgaact tgttttttac cggcaccacc gtttgggcag gtaatcatga acgtgagtat   1080
tatgccaaac agcagattaa tgtgattaat aatgcgatta atgaaagctc tccgcattat   1140
ctgggtaata gctatgacct gttttttaaa ggtcatccgg gtggtggtat tattaatacc   1200
ctgattatgc agaattatcc gagcatggtt gatattccga gcaaaatttc ctttgaagtg   1260
ctgatgatga ccgatatgct gccggatgca gttgcaggta ttgcaagcag cctgtatttt   1320
accattccgg cagaaaaaat caaatttatt gtgtttacca gcaccgaaac cattaccgat   1380
cgtgaaaccg cactgcgttc tccgctggtt caggttatga ttaaactggg cattgtgaag   1440
gaggaaaacg tcctgttttg ggcactcgag caccaccacc accaccactg agatccggct   1500
gctaacaaag cccgaaag                                                  1518
```

<210> SEQ ID NO 23
<211> LENGTH: 487
<212> TYPE: PRT
<213> ORGANISM: Artificial Sequence
<220> FEATURE:
<223> OTHER INFORMATION: Synthetic Psp26ST(15-501) WILD TYPE

<400> SEQUENCE: 23

```
Cys Asn Asn Ser Glu Glu Asn Thr Gln Ser Ile Ile Lys Asn Asp Ile
  1               5                  10                  15

Asn Lys Thr Ile Ile Asp Glu Glu Tyr Val Asn Leu Glu Pro Ile Asn
             20                  25                  30

Gln Ser Asn Ile Ser Phe Thr Lys His Ser Trp Val Gln Thr Cys Gly
         35                  40                  45

Thr Gln Gln Leu Leu Thr Glu Gln Asn Lys Glu Ser Ile Ser Leu Ser
     50                  55                  60

Val Val Ala Pro Arg Leu Asp Asp Glu Lys Tyr Cys Phe Asp Phe
 65                  70                  75                  80

Asn Gly Val Ser Asn Lys Gly Glu Lys Tyr Ile Thr Lys Val Thr Leu
                 85                  90                  95

Asn Val Val Ala Pro Ser Leu Glu Val Tyr Val Asp His Ala Ser Leu
            100                 105                 110

Pro Thr Leu Gln Gln Leu Met Asp Ile Ile Lys Ser Glu Glu Asn
        115                 120                 125

Pro Thr Ala Gln Arg Tyr Ile Ala Trp Gly Arg Ile Val Pro Thr Asp
    130                 135                 140

Glu Gln Met Lys Glu Leu Asn Ile Thr Ser Phe Ala Leu Ile Asn Asn
145                 150                 155                 160

His Thr Pro Ala Asp Leu Val Gln Glu Ile Val Lys Gln Ala Gln Thr
                165                 170                 175

Lys His Arg Leu Asn Val Lys Leu Ser Ser Asn Thr Ala His Ser Phe
            180                 185                 190

Asp Asn Leu Val Pro Ile Leu Lys Glu Leu Asn Ser Phe Asn Asn Val
        195                 200                 205

Thr Val Thr Asn Ile Asp Leu Tyr Asp Asp Gly Ser Ala Glu Tyr Val
    210                 215                 220
```

Asn Leu Tyr Asn Trp Arg Asp Thr Leu Asn Lys Thr Asp Asn Leu Lys
225                 230                 235                 240

Ile Gly Lys Asp Tyr Leu Glu Asp Val Ile Asn Gly Ile Asn Glu Asp
            245                 250                 255

Thr Ser Asn Thr Gly Thr Ser Val Tyr Asn Trp Gln Lys Leu Tyr
        260                 265                 270

Pro Ala Asn Tyr His Phe Leu Arg Lys Asp Tyr Leu Thr Leu Glu Pro
        275                 280                 285

Ser Leu His Glu Leu Arg Asp Tyr Ile Gly Asp Ser Leu Lys Gln Met
    290                 295                 300

Gln Trp Asp Gly Phe Lys Lys Phe Asn Ser Lys Gln Gln Leu Phe
305                 310                 315                 320

Leu Ser Ile Val Asn Phe Asp Lys Gln Lys Leu Gln Asn Glu Tyr Asn
                325                 330                 335

Ser Ser Asn Leu Pro Asn Phe Val Phe Thr Gly Thr Val Trp Ala
            340                 345                 350

Gly Asn His Glu Arg Glu Tyr Tyr Ala Lys Gln Gln Ile Asn Val Ile
            355                 360                 365

Asn Asn Ala Ile Asn Glu Ser Ser Pro His Tyr Leu Gly Asn Ser Tyr
370                 375                 380

Asp Leu Phe Phe Lys Gly His Pro Gly Gly Gly Ile Ile Asn Thr Leu
385                 390                 395                 400

Ile Met Gln Asn Tyr Pro Ser Met Val Asp Ile Pro Ser Lys Ile Ser
                405                 410                 415

Phe Glu Val Leu Met Met Thr Asp Met Leu Pro Asp Ala Val Ala Gly
                420                 425                 430

Ile Ala Ser Ser Leu Tyr Phe Thr Ile Pro Ala Glu Lys Ile Lys Phe
            435                 440                 445

Ile Val Phe Thr Ser Thr Glu Thr Ile Thr Asp Arg Glu Thr Ala Leu
        450                 455                 460

Arg Ser Pro Leu Val Gln Val Met Ile Lys Leu Gly Ile Val Lys Glu
465                 470                 475                 480

Glu Asn Val Leu Phe Trp Ala
                485

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Trp Ser His Pro Gln Phe Glu Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Asp Tyr Lys Asp Asp Asp Lys
1               5

PHOTOBACTERIUM SP. ALPHA-2-6-SIALYLTRANSFERASE VARIANTS

CROSS-REFERENCES TO RELATED APPLICATIONS

The present application claims priority to U.S. Provisional Pat. Appl. No. 62/092,697, filed on Dec. 16, 2014, which application is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. GM094523 and HD065122, awarded by the National Institutes of Health. The Government has certain rights in this invention.

REFERENCE TO A "SEQUENCE LISTING," A TABLE, OR A COMPUTER PROGRAM LISTING APPENDIX SUBMITTED ON A COMPACT DISK n/a

The Sequence Listing written in file SubstituteSequence-Listing_076916-0962203.txt, created on Oct. 17, 2017, 53,545 bytes, machine format IBM-PC, MS-Windows operating system, is hereby incorporated by reference in its entirety for all purposes.

BACKGROUND OF THE INVENTION

Sialic acid (Sia)-containing structures in eukaryotic systems play important roles in a variety of physiological and pathological processes, including cell-cell interactions, inflammation, fertilization, viral infection, differentiation, malignancies, and cell signaling (see, e.g., Chen and Varki, ACS Chem. Biol. 2010, 5, 163-176; Traving and Schauer, Cell Mol. Life Sci. 1998, 54, 1330-1349; Schauer, Curr. Opin. Struct. Biol. 2009, 19, 507-514; Varki, Nature 2007, 446, 1023-1029). Among more than 50 different sialic acid structures that have been identified in nature, N-acetyl-neuraminic acid (Neu5Ac) is the most common and the most abundant sialic acid form. Sialyltransferases (EC 2.4.99.X) are key enzymes involved in the biosynthesis of these sialic acid-containing oligosaccharides and glycoconjugates (see, Harduin-Lepers, et al. Glycobiology 1995, 5, 741-758). They catalyze the transfer of a sialic acid residue from its activated sugar nucleotide donor cytidine 5'-monophosphate sialic acid (CMP-sialic acid) to an acceptor, usually a structure with a galactose (Gal), an N-acetylgalactosamine (GalNAc), an N-acetylglucosamine (GlcNAc), or another sialic acid residue. Various linkages including Siaα2-3Gal, Siaα2-6Gal/GalNAc/GlcNAc, Siaα2-8Sia, and Siaα2-9Sia can be formed. Bifunctional glycosyltransferases (SiaD) that are responsible for the formation of Neu5Ac-containing Neisseria meningitidis serogroups W-135 and Y capsular polysaccharides (CPSs) [-6Gal/Glcα1-4Neu5Acα2-]$_n$ have been grouped together with other glycosyltransferases in glycosyltransferase 4 (GT4) family in the Carbohydrate Activated enZyme (CAZy) database based on protein sequence homology (see, Bhattacharjee, et al. Can. J. Biochem. 1976, 54, 1-8; Campbell, et al. Biochem. J. 1997, 326, 929-939; Coutinho, et al. J. Mol. Biol. 2003, 328, 307-317). All other sialyltransferases reported to date have been grouped into five CAZy glycosyltransferase (GT) families (GT29, GT38, GT42, GT52, and GT80). All known eukaryotic sialyltransferases belong to a single CAZy GT29 family, while bacterial sialyltransferases are more spread out among CAZy GT families GT38, GT42, GT52, and GT80 (see, Li and Chen, Appl. Microbiol. Biotechnol. 2012, 94, 887-905; Audry, et al. Glycobiology 2011,21, 716-726).

Since bacterial sialyltransferases can be produced more easily as active forms in larger amounts in Escherichia coli expression systems and many of them have broader substrate specificities than their mammalian counterparts, they have been used as efficient catalysts in preparative and large scale synthesis of biologically important sialosides (see, Yamamoto, Mar. Drugs 2010, 8, 2781-2794; Yu and Chen, et al. Angew. Chem. Int. Ed. 2006, 45, 3938-3944). For example, multifunctional Pasteurella multocida α2-3-sialyltransferase 1 (PmST1) has been used as a powerful catalyst in the chemoenzymatic synthesis of diverse α2-3-linked sialosides (see, Yu and Chen, et al. J. Am. Chem. Soc. 2005, 127, 17618-17619). Photobacterium damselae α2-6-sialyltransferase (Pd2,6ST) has been applied in the synthesis of α2-6-linked sialosides and glycopeptides (see, Yu, Angew. Chem. Int. Ed. 2006, supra; Yamamoto, et al. Biosci. Biotechnol. Biochem. 1998, 62, 210-214; Kajihara, et al. Carbohydr. Res. 1999, 315, 137-141; Teo, et al. Adv. Synth. Catal. 2005, 347, 967-972; Yu and Chen, et al. Nat. Protoc. 2006, 1, 2485-2492). Campylobacter jejuni OH4384 α2-3/8-sialyltransferase (CstII) has been used for the synthesis of GD3 and GT1a ganglioside oligosaccharides (see, Gilbert, et al. Biol. Chem. 2000, 275, 3896-3906; Blixt, et al. Carbohydr. Res. 2005, 340, 1963-1972; Antoine, et al. Angew. Chem. Int. Ed. 2005, 44, 1350-1352; Cheng and Chen, et al. Glycobiology 2008, 18, 686-697; Yu and Chen, et al. J. Am. Chem. Soc. 2009, 131, 18467-18477).

Among sialic acid-containing biologically important sialosides, sialyl Tn antigens (Siaα2-6GalNAcα1-O-Ser/Thr) have been reported to correlate with the invasive and metastatic growth of carcinoma cells and are considered as a tumor-associated antigens for cancer vaccination development (Wu and Guo. Bioconj. Chem. 2006, 17, 1537-1544). In addition to conventional chemical methods for synthesis of sialyl Tn (STn) antigens, sialyltransferase-catalyzed glycosylation has been shown as a highly efficient approach. The present inventors previously identified recombinant Photobacterium sp. JH-ISH-224 α2-6-sialyltransferase Psp26ST(15-501)-His$_6$ as a more suitable α2-6-sialyltransferase than Pd2,6ST for catalyzing the formation of STn antigens from N-acetylgalactosamine (GalNAc)-containing glycosides such as GalNAcα2AA, GalNAcαOSer, and GalNAcαOThr as acceptor substrates (Ding and Chen, et al. Chem. Commun. 2011, 47, 8691-8693). Nevertheless, the efficiency of Psp26ST(15-501)-His$_6$ in sialylating α-GalNAc-terminated glycosides (Tn-antigens) is still much lower than sialylating β-galactosides. In addition, the expression level of soluble Psp2,6ST(15-501)-His$_6$ (25 mg L$^{-1}$) is not as high as Pd2,6ST (36 mg L$^{-1}$; see, Sun and Chen, et al. Biotechnology Letters 2008, 30, 671-676). Sialyltransferases exhibiting high expression yield and high catalytic efficiency are needed in order to expand synthetic methodology for preparation of STn antigens and other biologically important sialosides. The present invention addresses this and other needs.

BRIEF SUMMARY OF THE INVENTION

In a first aspect, the invention provides Photobacterium sp. JH-ISH-224 α2-6-sialyltransferase (Psp26ST) variants having amino acid residues 15-501 of the wild-type enzyme sequence and one or more point mutations. In certain embodiments, the variants comprise the amino acid sequence set forth in SEQ ID NO: 2, SEQ ID NO: 4, SEQ ID NO: 6, or SEQ ID NO: 8. In related aspects, the invention provides a polynucleotide sequence set forth in SEQ ID NO: 1, as well as expression cassettes, vectors, and host cells for expressing the Psp26ST(15-501) variants described herein.

In another aspect, the invention provides a method of synthesizing a sialylated product. The method includes forming a reaction mixture containing an acceptor glycoside, a sialic acid donor, and a Psp26ST(15-501) variant as described herein. The reaction mixture is formed under conditions sufficient to form the sialylated product. In some embodiments, the sialic acid donor is cytidine-5'-monophosphate sialic acid (CMP-sialic acid or CMP-Sia) or a derivative thereof. In some embodiments, the sialylated product is a sialyl Tn antigen.

DETAILED DESCRIPTION OF THE INVENTION

I. General

Figure 1:
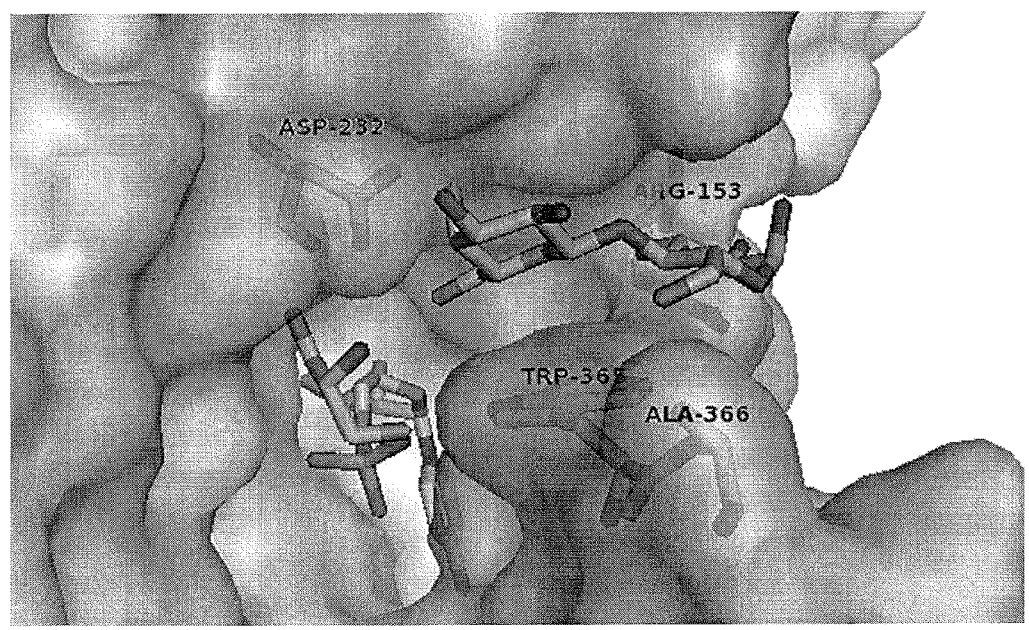
FIG. 1 shows the amino acid residues in the lactose-binding pocket of Psp26ST(15-501)-His$_6$. The protein structure was modeled based on the reported crystal structure of Δ16pspST6 (pdb: 2Z4T) and analyzed using PyMOL (carbon, nitrogen, oxygen, and phosphorus atoms in lactose and the amino acid residues of interests are shown as stick models).

The present invention is based on the discovery that the expression yield and catalytic efficiency of Photobacterium sp. JH-ISH-224 sialyltransferase can be improved by varying the amino acid sequence of the sialyltransferase. Protein crystal structure-based mutagenesis studies were carried out to improve the catalytic efficiency of Psp2,6ST(15-501)-His$_6$ for the formation of sialylated products such as STn antigens. Among several mutants obtained by altering the residues close to the acceptor substrate binding pocket of the enzyme, a mutant A366G with an elevated expression level (72-110 mg L$^{-1}$) and improved activity in catalyzing the formation of STn antigens from α-GalNAc-terminated glycosides was identified. The improved expression of the A366G mutant and W365 mutants was particularly unexpected, given the position of A366 residue close to the substrate binding pocket. The mutants can be used as improved catalysts in one-pot multienzyme (OPME) synthesis of STn sialosides. Exhibiting an improved expression level as well as enhanced activity, the Psp26ST(15-501)-His$_6$ A366G mutant is a particularly powerful catalyst for enzymatic and chemoenzymatic synthesis of α2-6-linked sialosides.

II. Definitions

The terms "peptide," "polypeptide," and "protein" are used interchangeably herein to refer to a polymer of amino acid residues. All three terms apply to naturally occurring amino acid polymers and non-natural amino acid polymers, as well as to amino acid polymers in which one (or more) amino acid residue is an artificial chemical mimetic of a corresponding naturally occurring amino acid. As used herein, the terms encompass amino acid chains of any length, including full-length proteins, wherein the amino acid residues are linked by covalent peptide bonds.

The terms "mutant" and "variant," in the context of sialyltransferases of the present invention, mean a polypeptide, typically recombinant, that comprises one or more amino acid substitutions relative to a corresponding, naturally-occurring or unmodified sialyltransferase.

The term "amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid).

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission. Nucleotides, as described herein, may also be referred to by their commonly accepted single-letter codes.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

The terms "amino acid modification" and "amino acid alteration" refer to a substitution, a deletion, or an insertion of one or more amino acids. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "nucleic acid," "nucleotide," and "polynucleotide" refer to deoxyribonucleic acids (DNA) or ribonucleic acids (RNA) and polymers. The term includes, but is not limited to, single-, double-, or multi-stranded DNA or RNA, genomic DNA, cDNA, and DNA-RNA hybrids, as well as other polymers comprising purine and/or pyrimidine bases or other natural, chemically modified, biochemically modified, non-natural, synthetic, or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)).

The terms "nucleotide sequence encoding a peptide" and "gene" refer to the segment of DNA involved in producing a peptide chain. In addition, a gene will generally include regions preceding and following the coding region (leader and trailer) involved in the transcription/translation of the gene product and the regulation of the transcription/translation. A gene can also include intervening sequences (introns) between individual coding segments (exons). Leaders, trailers, and introns can include regulatory elements that are necessary during the transcription and the translation of a gene (e.g., promoters, terminators, translational regulatory sequences such as ribosome binding sites and internal ribosome entry sites, enhancers, silencers, insulators, boundary elements, replication origins, matrix attachment sites and locus control regions, etc.). A "gene product" can refer to either the mRNA or protein expressed from a particular gene.

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

"Identical" and "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 75%, at least 80%, at least 85%, at least 90%, at least 95%, or at least 99% identical over a specified region), when compared and aligned for maximum correspondence over a comparison window, or designated region as measured using one of the following sequence comparison algorithms or by manual alignment and visual inspection. These definitions also refer to the complement of a nucleic acid test sequence.

"Similarity" and "percent similarity," in the context of two or more polypeptide sequences, refer to two or more sequences or subsequences that have a specified percentage of amino acid residues that are either the same or similar as defined by a conservative amino acid substitutions (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% similar over a specified region), when compared and aligned for maximum correspondence over a comparison window, or designated region as measured using one of the following sequence comparison algorithms or by manual alignment and visual inspection. Sequences are "substantially similar" to each other if, for example, they are at least 20%, at least 25%, at least 30%, at least 35%, at least 40%, at least 45%, at least 50%, or at least 55% similar to each other.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Additional examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA*, 90: 5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or peptides are substantially identical is that the peptide encoded by the first nucleic acid is immunologically cross reactive with the antibodies raised against the peptide encoded by the second nucleic acid. Thus, a peptide is typically substantially identical to a second peptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "transfection" and "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The terms "expression" and "expressed" in the context of a gene refer to the transcriptional and/or translational product of the gene. The level of expression of a DNA molecule in a cell may be determined on the basis of either the amount of corresponding mRNA that is present within the cell or the amount of protein encoded by that DNA produced by the cell.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

A polynucleotide/polypeptide sequence is "heterologous" to an organism or a second polynucleotide/polypeptide sequence if it originates from a different species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

The terms "vector" and "recombinant expression vector" refer to a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

As used herein, the term "glycosyltransferase" refers to a polypeptide that catalyzes the formation of an oligosaccharide from a nucleotide-sugar an acceptor sugar. Nucleotide-sugars include, but are not limited to, nucleotide diphosphate sugars (NDP-sugars) and nucleotide monophosphate sugars (NMP-sugars) such as a cytidine monophosphate sugar (CMP-sugar). In general, a glycosyltransferase catalyzes the transfer of the monosaccharide moiety of an NDP-sugar or CMP-sugar to a hydroxyl group of the acceptor sugar. The covalent linkage between the monosaccharide and the acceptor sugar can be a 1-3 linkage, a 1-4 linkage, a 1-6-linkage, a 1-2 linkage, a 2-3 linkage, a 2-6 linkage, a 2-8 linkage, or a 2-9 linkage as described above. The linkage may be in the $\alpha$- or $\beta$-configuration with respect to the anomeric carbon of the monosaccharide. Other types of linkages may be formed by the glycosyltransferases in the methods of the invention. Glycosyltransferases include, but are not limited to, heparosan synthases (HSs) glucosaminyltransferases, N-acetylglucosaminyltransferases, glucosyltransferasess, glucuronyltransferases, and sialyltransferases. The term "sialyltransferase" refers to an enzyme that catalyzes the transfer of a sialic acid residue from a sialic acid donor (e.g., a sialic acid nucleotide donor) to an acceptor such as an oligosaccharide, a polysaccharide, or a glycosylated protein.

As used herein, the term "oligosaccharide" refers to a compound containing at least two monosaccharides covalently linked together. Oligosaccharides include disaccharides, trisaccharides, tetrasaccharides, pentasaccharides, hexasaccharides, heptasaccharides, octasaccharides, and the like. Covalent linkages generally consist of glycosidic linkages (i.e., C—O—C bonds) formed from the hydroxyl groups of adjacent sugars. Linkages can occur between the 1-carbon and the 4-carbon of adjacent sugars (i.e., a 1-4 linkage), the 1-carbon and the 3-carbon of adjacent sugars (i.e., a 1-3 linkage), the 1-carbon and the 6-carbon of adjacent sugars (i.e., a 1-6 linkage), or the 1-carbon and the 2-carbon of adjacent sugars (i.e., a 1-2 linkage). Linkages can occur between the 2-carbon and the 3-carbon of adjacent sugars (i.e., a 2-3 linkage), the 2-carbon and the 6-carbon of adjacent sugars (i.e., a 2-6 linkage), the 2-carbon and the 8-carbon of adjacent sugars (i.e., a 2-8 linkage), or the 2-carbon and the 9-carbon of adjacent sugars (i.e., a 2-9 linkage). A sugar can be linked within an oligosaccharide such that the anomeric carbon is in the $\alpha$- or $\beta$-configuration. The oligosaccharides prepared according to the methods of the invention can also include linkages between carbon atoms other than the 1-, 2-, 3-, 4-, and 6-carbons or the 2-, 3-, 6-, 8-, and 9-carbons.

As used herein, the term "sialic acid" refers to N- and O-substituted derivatives of neuraminic acid (i.e., N- and O-substituted derivatives of 5-amino-2-keto-3,5-dideoxy-D-glycero-D-galactononulosonic acid—also referred to as (4S, 5R,6R,7S,8R)-5-amino-4,6,7,8,9-pentahydroxy-2-oxo-nonanoic acid). Sialic acids include, but are not limited to, N-acetyl neuraminic acid (Neu5Ac), N-glycolyl neuraminic acid (Neu5Gc), and 2-keto-3-deoxy-D-glycero-D-galactonononic acid (KDN), as well as O-acetyl, O-lactyl, O-methyl, O-sulfate and O-phosphate derivatives. As used herein, the term "sialylated product" refers to compound having a sugar moiety (e.g., a monosaccharide, an oligosaccharide, or a polysaccharide) and at least one sialic acid moiety covalently linked to the sugar moiety. The sialylated product can be, for example, a sialylated oligosaccharide, a sialylated polysaccharide, a sialylated glycopeptide, a sialylated glycoprotein, a sialylated glycolipid, or a sialylated natural product.

"Acceptor glycoside" refers to a substance (e.g., a glycosylated amino acid, a glycosylated protein, an oligosaccharide, or a polysaccharide) containing a sugar that accepts a sialic acid moiety from cytidine-5'-monophosphate sialic acid, or a derivative of, during a glycosylation (i.e., sialylation) reaction. The sugar of the acceptor glycoside can be a monosaccharide or an oligosaccharide as defined herein. In certain embodiments, the acceptor glycoside contains a galactosamine moiety, wherein the hydroxyl group at the anomeric carbon of the galactopyranose ring is the point of connection to the remainder of the glycoside. In some embodiments, the galactosamine moiety is an α-linked N-acetylgalactosamine moiety. A "glycosylated" protein/polypeptide refers to a protein/polypeptide having one or more monosaccharides, oligosaccharides, or polysaccharides bonded to the protein/polypeptide.

The term "Tn antigen" refers to GalNAcαSer and GalNAcαThr. In GalNAcαSer, "Ser" indicates serine or a serine-containing oligopeptide or polypeptide which is linked to the GalNAc moiety via a glycosidic bond from the hydroxyl group of the serine sidechain. In GalNAcαSer, "Thr" indicates threonine or a threonine-containing oligopeptide or polypeptide which is linked to the GalNAc moiety via a glycosidic bond from the hydroxyl group of the threonine sidechain. The polypeptide in a Tn antigen can be, but is not limited to, a mucin. Mucins are heavily O-glycosylated glycoproteins, including secreted glycoproteins and transmembrane cell surface glycoproteins. Mucins typically include repeated peptide stretches that are rich in serine or threonine O-glycan acceptor sites; these stretches have clustered O-glycans that can amount to 80% or more of the mucin by weight. Mucins can have hundreds of O-GalNAc glycans attached to serine or threonine residues, and the glycan clusters can cause a mucin to adopt an extended "bottle brush" conformation. A "sialylated Tn antigen," or "STn antigen," is a Tn antigen having a sialic acid bonded to the GalNAc moiety in the Tn antigen. Typically, the sialic acid in the STn antigen is linked to the GalNac moiety via an α2-6 glycosidic bond. STn antigen expression is limited on normal cells but is elevated on a wide range of cells of breast, prostate, pancreas, colorectal, lung, gastric, and ovarian cancers.

As used herein, the term "kinase" refers to a polypeptide that catalyzes the covalent addition of a phosphate group to a substrate. The substrate for a kinase used in the methods of the invention is generally a sugar as defined above, and a phosphate group is added to the anomeric carbon (i.e. the "1" position) of the sugar. The product of the reaction is a sugar-1-phosphate. Kinases include, but are not limited to, N-acetylhexosamine 1-kinases (NahKs), glucuronokinases (GlcAKs), glucokinases (GlcKs), galactokinases (GalKs), monosaccharide-1-kinases, and xylulokinases. Certain kinases utilize nucleotide triphosphates, including adenosine-5'-triphosphate (ATP) as substrates.

As used herein, the term "dehydrogenase" refers to a polypeptide that catalyzes the oxidation of a primary alcohol. In general, the dehyrogenases used in the methods of the invention convert the hydroxymethyl group of a hexose (i.e. the C6-OH moiety) to a carboxylic acid. Dehydrogenases useful in the methods of the invention include, but are not limited to, UDP-glucose dehydrogenases (Ugds).

As used herein, the term "nucleotide-sugar pyrophosphorylase" refers to a polypeptide that catalyzes the conversion of a sugar-1-phosphate to a UDP-sugar. In general, a uridine-5'-monophosphate moiety is transferred from uridine-5'-triphosphate to the sugar-1-phosphate to form the UDP-sugar. Examples of nucleotide-sugar pyrophosphorylases include glucosamine uridylyltransferases (GlmUs) and glucose-1-phosphate uridylyltransferases (GalUs). Nucleotide-sugar pyrophosphorylases also include promiscuous UDP-sugar pyrophosphorylases, termed "USPs," that can catalyze the conversion of various sugar-1-phosphates to UDP-sugars including UDP-Glc, UDP-GlcNAc, UDP-GlcNH$_2$, UDP-Gal, UDP-GalNAc, UDP-GalNH$_2$, UDP-Man, UDP-ManNAc, UDP-ManNH$_2$, UDP-GlcA, UDP-IdoA, UDP-GalA, and their substituted analogs.

As used herein, the term "pyrophosphatase" (abbreviated as PpA) refers to a polypeptide that catalyzes the conversion of pyrophosphate (i.e., $P_2O_7^{4-}$, $HP_2O_7^{3-}$, $H_2P_2O_7^{2-}$, $H_3P_2O_7^-$) to two molar equivalents of inorganic phosphate (i.e., $PO_4^{3-}$, $HPO_4^{2-}$, $H_2PO_4^-$).

As used herein, the term "CMP-sialic acid synthetase" refers to a polypeptide that catalyzes the synthesis of cytidine monophosphate sialic acid (CMP-sialic acid) from cytidine triphosphate (CTP) and sialic acid.

As used herein, the term "sialic acid aldolase" refers to an aldolase that catalyzes a reversible reaction that converts a suitable hexosamine, hexose, pentose, or derivative (such as N-acetyl mannosamine) to sialic acid via reaction with pyruvate.

III. Psp26ST Variants

In a first aspect, the invention provides *Photobacterium* sp. JH-ISH-224 α2-6-sialyltransferase (Psp26ST) variants having enhanced catalytic activity and/or increased expression levels with respect to the wild-type enzyme. In general, the Psp26ST variants include amino acid residues 15-501 of the wild-type enzyme sequence with one or more point mutations. Accordingly, certain embodiments of the invention provide an isolated polypeptide comprising the amino acid sequence set forth in SEQ ID NO: 2, SEQ ID NO: 4, SEQ ID NO: 6, or SEQ ID NO: 8.

In some embodiments, the invention provides an isolated Psp26ST(15-501) polypeptide having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the amino acid sequences set forth in SEQ ID NO: 2, 4, 6, or 8. In some embodiments, the polypeptide comprises the amino acid sequence set forth in SEQ ID NO: 2, SEQ ID NO: 4, or SEQ ID NO: 6. In some embodiments, the polypeptide comprises the amino acid sequence set forth in SEQ ID NO: 2. In some embodiments, the polypeptide comprises the amino acid sequence set forth in SEQ ID NO: 4. In some embodiments, the polypeptide comprises the amino acid sequence set forth in SEQ ID NO: 6. In some embodiments, the polypeptide comprises the amino acid sequence set forth in SEQ ID NO: 8.

In some embodiments, the polypeptide further comprises one or more heterologous amino acid sequences located at the N-terminus and/or the C-terminus of the polypeptide. The polypeptide can contain a number of heterologous sequences that are useful for expressing, purifying, and/or using the polypeptide. The polypeptide can contain, for example, a poly-histidine tag (e.g., a His$_6$ tag); a calmodulin-binding peptide (CBP) tag; a NorpA peptide tag; a Strep tag (e.g., Trp-Ser-His-Pro-Gln-Phe-Glu-Lys, SEQ ID NO: 24) for recognition by/binding to streptavidin or a variant thereof; a FLAG peptide (i.e., Asp-Tyr-Lys-Asp-Asp-Asp-Asp-Lys SEQ ID NO: 25) for recognition by/binding to anti-FLAG antibodies (e.g., M1, M2, M5); a glutathione S-transferase (GST); or a maltose binding protein (MBP) polypeptide. In some embodiments, the invention provides an isolated polypeptide comprising the amino acid sequence set forth in SEQ ID NO: 2, SEQ ID NO: 4, SEQ ID NO: 6, or SEQ ID NO: 8 with a His$_6$ peptide fused to the C-terminal residue of the amino acid sequence. In some embodiments, the polypeptide comprises the amino acid sequence set forth in SEQ ID NO: 2 with a His$_6$ peptide fused to the C-terminal residue of the amino acid sequence.

Recombinant Nucleic Acids

In a related aspect, the invention provides nucleic acids encoding Psp26ST variants as described herein. The nucleic acids can be generated from a nucleic acid template encoding the wild-type Psp26ST, using a number of recombinant DNA techniques that are known to those of skill in the art. Accordingly, certain embodiments of the invention provide an isolated nucleic acid comprising a polynucleotide sequence encoding a polypeptide comprising the amino acid sequence set forth in SEQ ID NO: 2, SEQ ID NO: 4, SEQ ID NO: 6, or SEQ ID NO: 8. In some embodiments, the isolated nucleic acid comprises a polynucleotide sequence encoding a polypeptide comprising the amino acid sequence set forth in SEQ ID NO: 2, SEQ ID NO: 4, or SEQ ID NO: 6. In some embodiments, the isolated nucleic acid comprises a polynucleotide sequence encoding a polypeptide comprising the amino acid sequence set forth in SEQ ID NO: 2.

In some embodiments, the invention provides an isolated Psp26ST(15-501) nucleic acid having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the nucleic acid sequences set forth in SEQ ID NO: 1, 3, 5, or 7. In some embodiments, the isolated nucleic acid comprises the polynucleotide sequence set forth in SEQ ID NO: 1, SEQ ID NO: 3, SEQ ID NO: 5, or SEQ ID NO: 7. In some embodiments, the isolated nucleic acid comprises the polynucleotide sequence set forth in SEQ ID NO: 1, SEQ ID NO: 3, or SEQ ID NO: 5. In some embodiments, the isolated nucleic acid comprises the polynucleotide sequence set forth in SEQ ID NO: 1.

Using a Psp26ST nucleic acid of the invention, a variety of expression constructs and vectors can be made. Generally, expression vectors include transcriptional and translational regulatory nucleic acid regions operably linked to the nucleic acid encoding the mutant sialyltransferase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retro-regulatory Element (PRE) to enhance the half-life of the transcribed mRNA (see, Gelfand et al. U.S. Pat. No. 4,666,848). The transcriptional and translational regulatory nucleic acid regions will generally be appropriate to the host cell used to express the sialyltransferase. Numerous types of appropriate expression vectors and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. Typically, the regulatory sequences will include a promoter and/or transcriptional start and stop sequences. Vectors also typically include a polylinker region containing several restriction sites for insertion of foreign DNA. As described above, heterologous sequences (e.g., a fusion tag such as a His tag) can be used to facilitate purification and, if desired, removed after purification. The construction of suitable vectors containing DNA encoding replication sequences, regulatory sequences, phenotypic selection genes, and the mutant sialyltransferase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)).

Accordingly, some embodiments of the invention provide an expression cassette comprising a Psp26ST nucleic acid as described herein operably linked to a promoter. In some embodiments, the invention provides a vector comprising a Psp26ST nucleic acid as described herein. In some embodiments, the Psp26ST nucleic acid in the expression cassette or vector encodes a polypeptide comprising the amino acid sequence set forth in SEQ ID NO: 2, SEQ ID NO: 4, SEQ ID NO: 6, or SEQ ID NO: 8. In some embodiments, the Psp26ST nucleic acid in the expression cassette or vector encodes a polypeptide comprising the amino acid sequence set forth in SEQ ID NO: 2. In some embodiments, the Psp26ST nucleic acid in the expression cassette or vector comprises the polynucleotide sequence set forth in SEQ ID NO: 1, SEQ ID NO: 3, SEQ ID NO: 5, or SEQ ID: 7. In some embodiments, the Psp26ST nucleic acid in the expression cassette or vector comprises the polynucleotide sequence set forth in SEQ ID NO: 1.

Host Cells

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a sialyltransferase of the invention is introduced into a cell, either alone or in combination with a vector. By "introduced into," it is meant that the nucleic acids enter the cells in a manner suitable for subsequent integration, amplification, and/or expression of the nucleic acid. The method of introduction is largely dictated by the targeted cell type. Exemplary methods include CaPO$_4$ precipitation, liposome fusion, LIPOFECTIN® transfection reagent (i.e., a 1:1 (w/w) liposome formulation of the cationic lipid N-[1-(2,3-dioleyloxy)propyl]-n,n,n-trimethylammonium chloride and dioleoyl phophotidylethanolamine in membrane-filtered water), electroporation, heat shock, viral infection, and the like.

In some embodiments, prokaryotes are used as host cells for the initial cloning steps of the present invention. Other host cells include, but are not limited to, eukaryotic (e.g., mammalian, plant and insect cells), or prokaryotic (bacterial) cells. Exemplary host cells include, but are not limited to, *Escherichia coli*, *Saccharomyces cerevisiae*, *Pichia pastoris*, Sf9 insect cells, and CHO cells. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; and other strains of *E. coli*, such as HB101, JM101, NM522, NM538, and NM539. Many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.*, 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many other suitable vectors are available as well.

Accordingly, some embodiments of the invention provide a host cell comprising a Psp26ST nucleic acid, expression cassette, or vector, as described herein. In some embodiments, the Psp26ST nucleic acid, expression cassette, or vector in the host cell encodes a polypeptide comprising the amino acid sequence set forth in SEQ ID NO: 2, SEQ ID NO: 4, SEQ ID NO: 6, or SEQ ID NO: 8. In some embodiments, the Psp26ST nucleic acid, expression cassette, or vector in the host cell encodes a polypeptide comprising the amino acid sequence set forth in SEQ ID NO: 2. In some embodiments, the Psp26ST nucleic acid, expression cassette, or vector in the host cell comprises the polynucleotide sequence set forth in SEQ ID NO: 1, SEQ ID NO: 3, SEQ ID NO: 5, or SEQ ID: 7. In some embodiments, the Psp26ST nucleic acid, expression cassette, or vector in the host cell comprises the polynucleotide sequence set forth in SEQ ID NO: 1.

In some embodiments, the Psp26ST variants of the present invention are produced by culturing a host cell transformed with an expression vector containing a nucleic acid encoding the sialyltransferase, under the appropriate conditions to induce or cause expression of the sialyltransferase. Methods of culturing transformed host cells under conditions suitable for protein expression are well-known in the art (see, e.g., Sambrook et al., supra). Suitable host cells for production of the Psp26ST variants from lambda pL promoter-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Suitable host cells for production of the Psp26ST variants from T7 promoter-containing plasmid vectors include *E. coli* strain BL21 (DE3) and related lysogens (see, e.g., U.S. Pat. No. 5,693,489). Following expression, a Psp26ST variant can be harvested and isolated. In some embodiments, the present invention provides a cell including a recombinant nucleic acid of the present invention. The cells can be prokaryotic or eukaryotic. The cells can be mammalian, plant, bacteria, or insect cells.

IV. Methods for Synthesizing Sialylated Products

The Psp26ST variants of the present invention can be used to prepare oligosaccharides and other glycosylated products, specifically to add N-acetylneuraminic acid (Neu5Ac), other sialic acids, and analogs thereof, to acceptor glycosides. For example, Psp26ST(15-501)-His$_6$ A366G can catalyze the transfer of Neu5Ac from CMP-Neu5Ac to a GalNAc moiety in an acceptor glycoside.

Accordingly, another aspect of the present invention provides a method of synthesizing a sialylated product. The method includes forming a reaction mixture containing an acceptor glycoside, a sialic acid donor, and a Psp26ST variant as described herein, under conditions sufficient to form the sialylated product. In certain embodiments, the Psp26ST variant is a polypeptide comprising the amino acid sequence set forth in SEQ ID NO: 2, SEQ ID NO: 4, SEQ ID NO: 6, or SEQ ID NO: 8. In some embodiments, the sialylated product is a sialylated oligosaccharide, a sialylated polysaccharide, a sialylated glycopeptide, or a sialylated glycoprotein.

Any suitable acceptor glycoside can be used in the methods of the invention. Typically, the acceptor glycoside will contain a GalNAc moiety as shown in Formula I:

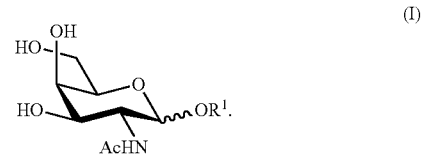

(I)

In acceptor glycosides of Formula I, R$^1$ can be a monosaccharide, an oligosaccharide, a polysaccharide, an amino acid, an oligopeptide, or a polypeptide. Other R$^1$ groups, e.g., fluorophore-containing R$^1$ groups, can also be present in the acceptor glycosides, as described in more detail below. The acceptor glycoside can contain an α-linked GalNAc moiety, as shown in Formula Ia:

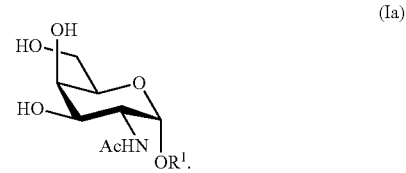

(Ia)

Alternatively, the acceptor glycoside can contain a β-linked GalNAc moiety, as shown in Formula Ib:

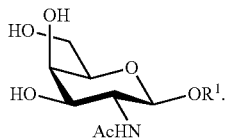
(Ib)

In some embodiments, the acceptor glycoside has a structure according to the formula:

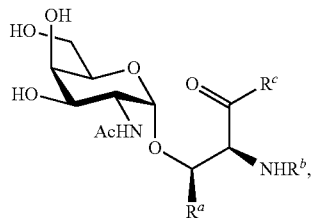

or a salt thereof, wherein:
$R^a$ is selected from the group consisting of H and $CH_3$,
$R^b$ is selected from the group consisting of H, an amino acid residue, an oligopeptide residue, and a polypeptide residue,
$R^c$ is selected from the group consisting of OH, an amino acid residue, an oligopeptide residue, and a polypeptide residue.

The sialic acid donor of the present invention includes a nucleotide and a sialic acid moiety. Suitable nucleotides include, but are not limited to, adenine, guanine, cytosine, uracil and thymine nucleotides with one, two or three phosphate groups. In some embodiments, the nucleotide can be cytidine monophosphate (CMP). The sialic acid donor can contain a number of sialic acid moieties. Sialic acid is a general term for N- and O-substituted derivatives of neuraminic acid, and includes, but is not limited to, N-acetyl (Neu5Ac) or N-glycolyl (Neu5Gc) derivatives, as well as O-acetyl, O-lactyl, O-methyl, O-sulfate and O-phosphate derivatives. In some embodiments, the sialic acid can be a compound of the formula:

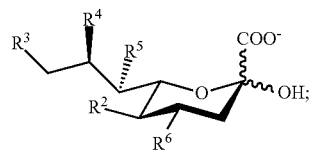

wherein $R^2$ is selected from H, OH, $N_3$, NHC(O)Me, NHC(O)CH$_2$OH, NHC(O)CH$_2$N$_3$, NHC(O)OCH$_2$C≡CH, NHC(O)CH$_2$F, NHC(O)CH$_2$NHCbz, NHC(O)CH$_2$OC(O)Me, and NHC(O)CH$_2$OBn; and $R^3$, $R^4$, $R^5$, and $R^6$ are independently selected from H, OH, $N_3$, OMe, F, $OSO_3^-$, $OPO_3H^-$, and OC(O)Me. In some embodiments, the sialic acid donor is a cytidine 5'-monophosphate-sialic acid (CMP-sialic acid or CMP-Sia), or a derivative thereof. In some embodiments, the CMP-sialic acid is cytidine 5'-monophosphate N-acetylneuraminic acid (CMP-Neu5Ac) or a CMP-Neu5Ac analog. Other donor substrates are useful in the methods of the present invention. In some embodiments, the sialic acid is a compound of the formula:

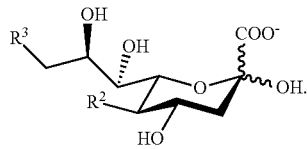

In some embodiments, the sialic acid donor is a compound of the formula:

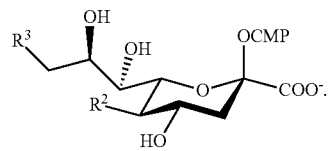

The methods of the invention include providing reaction mixtures that contain the Psp26ST variants described herein. The Psp26ST variants can be, for example, isolated or otherwise purified prior to addition to the reaction mixture. As used herein, a "purified" enzyme (e.g., a Psp26ST variant, a CMP-sialic acid synthetase, or a sialic acid aldolase) refers to an enzyme which is provided as a purified protein composition wherein the enzyme constitutes at least about 50% of the total protein in the purified protein composition. For example, the enzyme (e.g., a Psp26ST variant) can constitute about 50%, 60%, 70%, 75%, 80%, 85%, 90%, 95%, or 99% of the total protein in the purified protein composition. In some embodiments, the Psp26ST variant in the reaction mixture is provided as a purified protein composition wherein the Psp26ST variant constitutes at least about 95% of the total protein in purified protein composition. The amount of the Psp26ST variant in a purified protein composition can be determined by any number of known methods including, for example, by polyacrylamide gel electrophoresis (e.g., SDS-PAGE) followed by detection with a staining reagent (e.g., Coomassie Brilliant Blue G-250, a silver nitrate stain, and/or a reagent containing a Psp26ST antibody). The Psp26ST variants and other enzymes used in the methods of the invention can also be secreted by a cell present in the reaction mixture. Alternatively, a Psp26ST variant or another enzyme can catalyze the reaction within a cell expressing the variant.

Reaction mixtures can contain additional reagents for use in glycosylation techniques. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, CaCl$_2$, and salts of Mn$^{2+}$ and Mg$^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[Bis(carboxymethyl)amino]ethyl}(carboxymethyl) amino)acetic acid (EDTA), and 1,2-bis(o-aminophenoxy) ethane-N,N,N',N'-tetraacetic acid (BAPTA)), reducing agents (e.g., dithiothreitol (DTT), β-mercaptoethanol (BME), and tris(2-carboxyethyl)phosphine (TCEP)), and labels (e.g., fluorophores, radiolabels, and spin labels). Buffers, cosolvents, salts, detergents/surfactants, chelators, reducing agents, and labels can be used at any suitable concentration, which can be readily determined by one of skill in the art. In general, buffers, cosolvents, salts, detergents/surfactants, chelators, reducing agents, and labels are included in reaction mixtures at concentrations ranging from about 1 µM to about 1 M. For example, a buffer, a cosolvent, a salt, a detergent/surfactant, a chelator, a reducing agent, or a label can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, the reaction mixtures in the methods of the invention contain an acceptor glycoside, a sialic acid donor, and a Psp26ST variant as described herein, and one or more components selected from a buffer, a cosolvent, a salt, a detergent/surfactant, a chelator, a reducing agent, and a label. In some embodiments, the reaction mixtures in the methods of the invention contain an acceptor glycoside, a sialic acid donor, and a Psp26ST variant as described herein, and one or more components selected from a buffer, a cosolvent, a salt, a detergent/surfactant, a chelator, and a reducing agent. In some embodiments, the reaction mixtures in the methods of the invention consist essentially of an acceptor glycoside, a sialic acid donor, and a Psp26ST variant as described herein, and one or more components selected from a buffer, a cosolvent, a salt, a detergent/surfactant, a chelator, and a reducing agent.

Reactions are conducted under conditions sufficient to transfer the sialic acid moiety from the sialic acid donor to the acceptor glycoside. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time.

In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of a particular Psp26ST variant, sialic acid donor, or acceptor glycoside.

The sialic acid donor can be prepared prior to forming the sialylated product, or prepared in situ immediately prior to formation of the sialylated product. In some embodiments, the methods of the present invention also include forming a reaction mixture including a CMP-sialic acid synthetase, cytidine triphosphate, and N-acetylneuraminic acid (Neu5Ac) or a Neu5Ac analog, under conditions suitable to form CMP-Neu5Ac or a CMP-Neu5Ac analog. Any suitable CMP-sialic acid synthetase (i.e., N-acetylneuraminate cytidylyltransferase, EC 2.7.7.43) can be used in the methods of the invention. For example, CMP-sialic acid synthetases from *E. coli*, *C. thermocellum*, *S. agalactiae*, *P. multocida*, *H. ducreyi*, or *N. meningitidis* can be used. In some embodiments, the CMP-sialic acid synthetase is a purified CMP-sialic acid synthetase as described above. Other components (e.g., buffers, cosolvents, salts, detergents/surfactants, chelators, and/or reducing agents, as described above) can be included in the reaction mixture for forming the CMP-Neu5Ac/CMP-Neu5Ac analog. In some embodiments, the step of forming the sialic acid donor and the step of forming the sialylated product are performed in one pot.

In some embodiments, the sialic acid moiety of the sialic acid donor is prepared separately prior to use in the methods of the present invention. Alternatively, the sialic acid moiety can be prepared in situ immediately prior to use in the methods of the invention. In some embodiments, the methods of the invention include forming a reaction mixture including a sialic acid aldolase, pyruvic acid or derivatives thereof, and N-acetylmannosamine or derivatives thereof, under conditions suitable to form Neu5Ac or a Neu5Ac analog. Any suitable sialic acid aldolase (i.e., N-acetylneuraminate pyruvate lyase, EC 4.1.3.3) can be used in the methods of the invention. For example, sialic acid aldolases from *E. coli*, *L. plantarum*, *P. multocida*, or *N. meningitidis* can be used. In some embodiments, the sialic acid aldolase is a purified sialic acid aldolase as described above. Other components (e.g., buffers, cosolvents, salts, detergents/surfactants, chelators, and/or reducing agents, as described above) can be included in the reaction mixture for forming the Neu5Ac/Neu5Ac analog. In some embodiments, the step of forming the sialic acid moiety, the step of forming the sialic acid donor, and the step of forming the sialylated product are performed in one pot.

The products prepared by the methods of the invention can include a variety of sialylated oligosaccharides, sialylated polysaccharides, sialylated glycopeptide, and sialylated glycoproteins. In some embodiments, the sialylated product comprises a sialylated α-linked GalNAc moiety. In some embodiments, the sialylated α-linked GalNAc moiety is a Neu5Acα2-6GalNAc moiety.

In some embodiments, the sialylated product is a sialyl Tn antigen. In some such embodiments, the acceptor glycoside has a structure according to the formula:

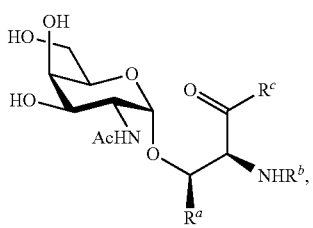

or a salt thereof, wherein:

$R^a$ is selected from the group consisting of H and $CH_3$, $R^b$ is selected from the group consisting of H, an amino acid residue, an oligopeptide residue, and a polypeptide residue, and $R^c$ is selected from the group consisting of OH, an amino acid residue, an oligopeptide residue, and a polypeptide residue.

In some embodiments, the sialyl Tn antigen has a structure according to the formula:

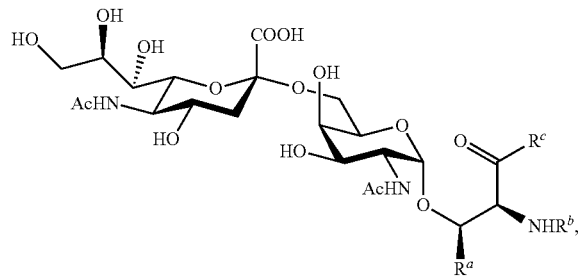

or a salt thereof, wherein:

$R^a$ is selected from the group consisting of H and $CH_3$, $R^b$ is selected from the group consisting of H, an amino acid residue, an oligopeptide residue, and a polypeptide residue, $R^c$ is selected from the group consisting of OH, an amino acid residue, an oligopeptide residue, and a polypeptide residue.

In some embodiments, $R^b$ and $R^c$ are independently selected polypeptide residues. That is, the sialyl Tn antigen contains a Neu5Acα2-6GalNAc moiety bonded to a serine or threonine residue in a polypeptide chain. In some such embodiments, $R^b$ and $R^c$ are optionally and independently glycosylated.

V. Examples

Example 1. Psp26ST(15-501)-$His_6$ Activity and Psp26ST(15-501)-$His_6$ Mutants

Procedure for Psp26ST(15-501)-$His_6$ Sialylation Assay with Periodic Addition of CMP-Neu5Ac Two reactions were set up at 20° C. in MES buffer (200 mM, pH 5.0) containing Psp2,6ST(15-501)-$His_6$ (6.0 μM), CMP-Neu5Ac (1 mM), and GalNAcα2AA (1 mM) in a total volume of 50 μL. One of the reactions was used as a control and was incubated for 4 h. The other was incubated for 1 h, 2 equivalents of CMP-Neu5Ac was then added. The same dose was added every hour for up to 4 h reaction duration. Aliquots (2 μL each) were withdrawn and the reactions were stopped by adding 10 μL of cold ethanol followed by centrifugation. The samples were diluted and kept on ice until aliquots of 8 μL were injected and analyzed by a Shimadzu LC-6AD system equipped with a membrane on-line degasser, a temperature control unit, and a fluorescence detector (Shimadzu RF-10AXL). A reverse-phase Premier C18 column (250×4.6 mm i.e., 5 μm particle size, Shimadzu) protected with a C18 guard column cartridge was used. The mobile phase was 25% acetonitrile in water. The 2-aminobenzoic acid (2AA)-labeled fluorescent acceptor and the product formed were detected with excitation at 315 nm and emission at 400 nm.

Procedure for Kinetic Analysis of Donor Hydrolysis by $His_6$-Pd2,6ST(16-497), Psp26ST(15-501)-$His_6$ and its A235D and A366G Mutants The kinetics study for the donor hydrolysis activity of $His_6$-Pd2,6ST(16-497) was carried out at 37° C. for 20 min in Tris-HCl buffer (200 mM, pH 8.0). The kinetics study for the donor hydrolysis activities of Psp26ST(15-501)-$His_6$ and its A235D mutant was carried out at 20° C. for 10 min in Tris-HCl buffer (200 mM, pH 8.0). All reactions were performed in duplicate in a total volume of 10 μL containing varied concentrations of CMP-Neu5Ac (10, 20, 40, 60, 80 and 100 mM) and the enzyme (6 μM). Reactions were stopped by adding 10 μL of ethanol and then centrifuged. The supernatants were analyzed by a P/ACETM capillary electrophoresis (CE) system equipped with a photodiode array (PDA) detector (Beckman Coulter, Inc., Fullerton, Calif.). CE conditions were as follows: 75 μm i.d. capillary, 25 KV/80μÅ, 5 s vacuum injections, monitored at 200 nm and 254 nm, the running buffer used was sodium tetraborate (25 mM, pH 9.4). Apparent kinetic parameters were obtained by fitting the experimental data (the average values of duplicate assay results) into the Michaelis-Menten equation using Grafit 5.0.

Results.

The tertiary crystal structure of Δ16Psp26ST in complex with CMP and lactose (pdb: 2Z4T) showed that residues Arg153, Trp365, and Ala366 help to define a relatively narrow pocket for the acceptor substrate (lactose) of the enzyme (FIG. 1; see also, Kakuta, et al. *Glycobiology* 2008, 18, 66-73). This contributes to the enzyme's preference towards n-linked galactosides as acceptor substrates (see, Ding, 2011, supra). In order to accommodate acceptors terminated with an α-linked N-acetylgalactosamine residue such as Tn antigens, mutating Arg153, Trp365, and Ala366 to smaller amino acid residues was proposed. For this purpose, R153G, W365A, W365G, W365S, and A366G were designed.

Figure 2A:
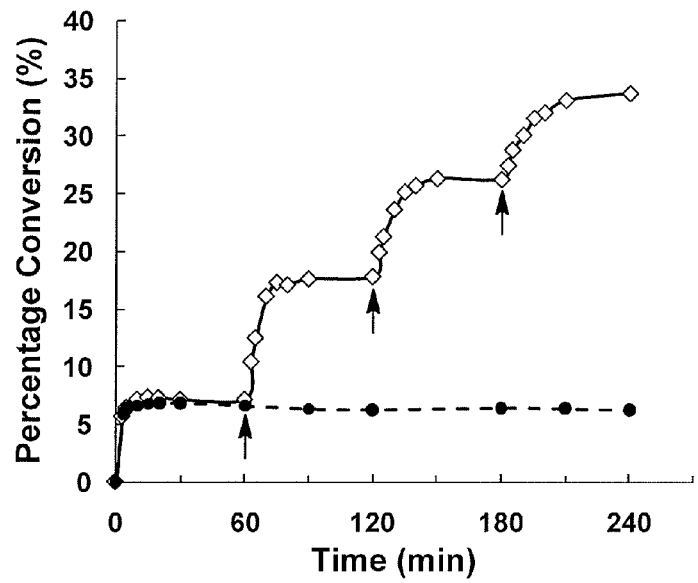
FIG. 2A shows a time course study for the donor hydrolysis activity of Psp26ST(15-501)-His$_6$, where GalNAcα2AA was used as an acceptor with periodic addition of 2 equivalents of CMP-Neu5Ac (shown by arrows).
Figure 2B:
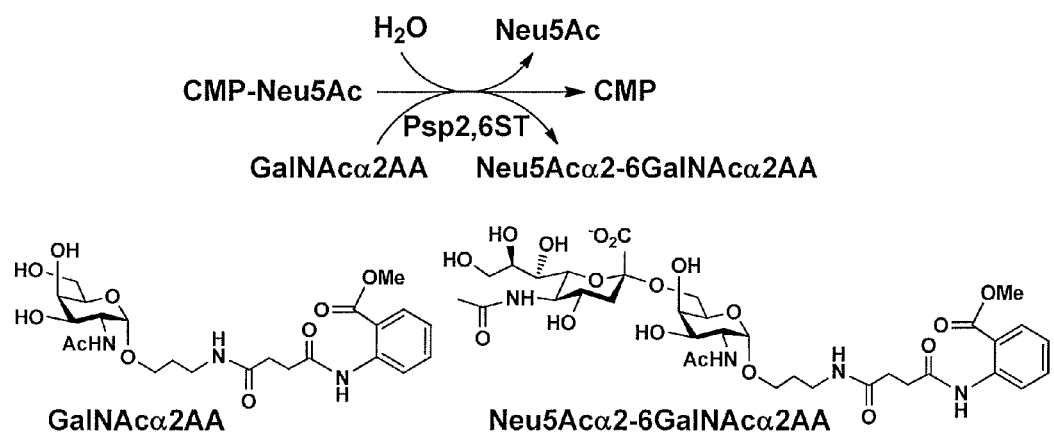
FIG. 2B shows a schematic illustration of donor hydrolysis of Psp26ST(15-501)-His$_6$, where water competes with the GalNAcα2AA acceptor in the Psp26ST(15-501)-His$_6$-catalyzed sialylation reaction.

Donor hydrolysis activity of glycosyltransferases has been previously shown to compete with the glycosylation process and lead to low glycosylation yields if a poor glycosyltransferase acceptor substrate is used (see, Sugiarto and Chen, et al. *ACS Chem. Biol.* 2012, 7, 1232-1240). Indeed, when GalNAcα2AA was used as an acceptor for Psp26ST(15-501)-$His_6$, adding one equivalent of CMP-Neu5Ac led to the formation of only 7.3% of sialylated product Neu5Acα2-6GalNAcα2AA and the reaction was completed in 15 min (FIG. 2A). A longer incubation time for up to 60 min (solid line marked with white diamonds in FIG. 2A) or 240 min (dashed line marked with black circles in FIG. 2A) did not improve the sialylation yield. When an additional two equivalents of CMP-Neu5Ac was added, the sialylation yield was improved to 17% in 15 min (solid line marked with white diamonds in FIG. 2A). Similarly, adding the third and the fourth doses (2 equivalents at each time) of CMP-Neu5Ac pushed the reaction yields to 25% and 33%, respectively (solid line marked with white diamonds in FIG. 2A). These results provided evidence that the donor hydrolysis activity of Psp26ST(15-501)-His$_6$, where water molecules compete with the GalNAcα2AA acceptor molecules (FIG. 2B), contribute to the relatively low yields of GalNAcα2AA α2-6-sialylation reactions.

Figure 3:
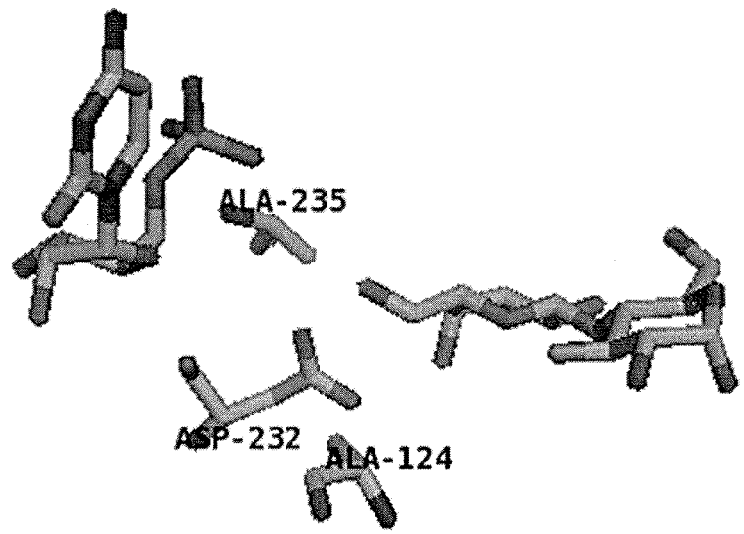
FIG. 3 shows the amino acid residues in close proximity to the catalytic base (Asp232) of Psp26ST(15-501)-His$_6$. The protein structure was modeled based on the reported crystal structure of Δ16pspST6 (pdb: 2Z4T) and analyzed using PyMOL (carbon, nitrogen, oxygen, and phosphorus atoms in lactose and the amino acid residues of interests are shown as stick models).

Previous crystal structure-based mutagenesis studies of another CAZy GT80 family member PmST1 which shares 36% amino acid sequence identity with the sialyltransferase domain of Psp2,6ST showed that mutating a neutral amino acid residue (Met144) in a close proximity to the catalytic base Asp141 of PmST1 generated a mutant (PmST1 M144D) with decreased donor hydrolysis activity. See, Sugiarto, 2012, supra. The corresponding catalytic base is Asp232 and the corresponding residue for mutation is Ala235 in Psp26ST(15-501)-His$_6$ (FIG. 3). Therefore, Psp26ST(15-501)-His$_6$ A235D mutant was designed in the attempt to reduce the donor hydrolysis activity and to enhance the sialylation activity of the enzyme. Furthermore, another neutral amino acid residue Ala124 close to the catalytic Asp232 of Psp26ST(15-501)-His$_6$ as shown in the crystal structure was identified (FIG. 3), and the A124D mutant was also designed to test enhanced sialylation activity of the enzyme.

Example 2. Expression and Purification of Psp26ST(15-501)-His$_6$

Material.

*Escherichia coli* BL21 (DE3) was from Invitrogen (Carlsbad, Calif., USA). Nickel-nitrilotriacetic acid agarose (Ni$^{2+}$-NTA agarose) and QIAprep spin miniprep kit were from Qiagen (Valencia, Calif., USA). Bicinchoninic acid (BCA) protein assay kit was from Pierce Biotechnology, Inc. (Rockford, Ill.). QuikChange Multi Site-Directed Mutagenesis Kit was from Agilent Technologies company/Stratagene (Santa Clara, Calif.).

Site-Directed Mutagenesis.

Site-directed mutagenesis was carried out using the QuikChange Multi Site-Directed Mutagenesis Kit from Stratagene according to the protocol from the manufacturer. The primers (the sites for mutations are underlined) used are shown in Table 1.

TABLE 1

Primers used for site-directed mutagenesis.

| Mutant | Primer | SEQ ID NO |
|---|---|---|
| A366G | 5' GGCACCACCGTTTGG<u>GGT</u>GGTA ATCATGAACG 3' | 15 |
| W365G | 5' TTACCGGCACCACCGTT<u>GGC</u>GC AGGTAATCATGAACG 3' | 16 |
| W365A | 5' TTACCGGCACCACCGTT<u>GCC</u>GC AGGTAATCATGAACG 3' | 17 |
| W365S | 5' TTACCGGCACCACCGTT<u>AGC</u>GC AGGTAATCATGAACG 3' | 18 |
| R153G | 5' CGTTATATTGCATGGG<u>GGT</u>A TTGTTCCGACCGATGAG 3' | 19 |
| A124D | 5' GAAGTTTATGTTGATCAT<u>GAT</u>A GCCTGCCGACCCTGCAG 3' | 20 |
| A235D | 5' TCTGTATGACGATGGCAGC<u>GAT</u> GAGTACGTGAATCTGTATAAT 3' | 21 |

Mutation sites are underlined.

Protein Expression and Purification of Psp26ST(15-501)-His$_6$ and Mutants.

The plasmids containing mutant genes were transformed into *Escherichia coli* BL21 (DE3). The *Escherichia coli* cells were cultured in LB-rich media (10 g L$^{-1}$ tryptone, 5 g L$^{-1}$ yeast extract, and 10 g L$^{-1}$ NaCl) supplemented with ampicillin (100 μg mL$^{-1}$). Overexpression of the mutants was achieved by adding 0.3 mM of isopropyl-1-thio-β-D-galactopyranoside (IPTG) to the *Escherichia coli* culture when its OD$_{600\ nm}$ reached 0.8. The induced culture was incubated at 20° C. for 20 h with vigorous shaking at 250 rpm in a C25KC incubator shaker (New Brunswick Scientific, Edison, N.J.). His$_6$-tagged mutant proteins were purified from the cell lysate. To obtain cell lysate, the cell pellet harvested by centrifugation at 4000 rpm for 2 h was resuspended in 20 mL (for cells obtained from one liter culture) of lysis buffer (pH 8.0, 100 mM Tris-HCl containing 0.1% Triton X-100). Lysozyme (50 μg mL$^{-1}$) and DNaseI (3 μg mL$^{-1}$) were added to the resuspended cells followed by shaking at 37° C. for 60 min. The lysate was obtained as the supernatant after centrifugation at 11,000 rpm for 20 min. Purification of His$_6$-tagged proteins from the lysate was achieved using 10 mL column packed with Ni$^{2+}$-NTA agarose. The column was pre-equilibrated with 8 column volumes of binding buffer (5 mM imidazole, 0.5 M NaCl, 50 mM Tris-HCl pH 7.5). After loading the sample, the column was washed with 8 column volumes of the binding and 8 column volumes of washing buffer (20 mM imidazole, 0.5 M NaCl, 50 mM Tris-HCl pH 7.5). Protein was eluted using 8 column volumes of the elute buffer (200 mM imidazole, 0.5 M NaCl, 50 mM Tris-HCl pH 7.5). The fractions containing the purified enzyme were collected and stored at 4° C. Protein concentrations were quantified by bicinchoninic acid (BCA) protein assay kit according to manufacturer's instruction using bovine serum albumin (BSA) as the protein standard. The wild-type enzyme and A366G mutant were expressed, purified, and quantified in duplicates or triplets for at least three times.

Sodium Dodecylsulfate-Polyacrylamide Gel Electrophoresis (SDS-PAGE).

SDS-PAGE was performed in a 12% Tris-glycine gel using Bio-Rad Mini-protein III cell gel electrophoresis unit (Bio-Rad, Hercules, Calif.) at DC=150V. Bio-Rad Precision Plus Protein Standards (10-250 kD) were used as molecular weight standards. Gels were stained with Coomassie Blue. Cell lysates from the wild-type enzyme and the mutants were prepared exactly the same and the same volume (~30 mL) of the lysate was obtained for each construct. The same volume of the lysate was used to prepare samples for SDS-PAGE and the same volume (10 μL) was loaded to the gel.

Results.

Figure 4:
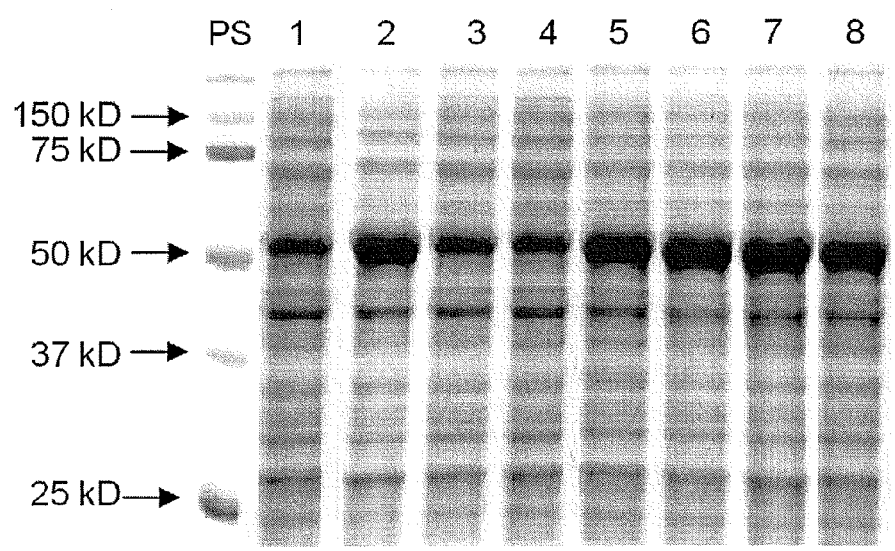
FIG. 4 shows the SDS-PAGE analysis of the expression of Psp2,6ST(15-501)-His$_6$ and its mutants in cell lysates. Lanes: PS, protein standards; 1, wild-type; 2, A366G mutant; 3, A235D mutant; 4, A124D mutant, 5, W365S mutant; 6, W365G mutant; 7, W365A mutant; 8, R153G mutant.

Sodium dodecyl sulfate polyacrylamide gel electrophoresis (SDS-PAGE) analysis of the lysates (FIG. 4) showed that all of the obtained Psp2,6ST(15-501)-His$_6$ mutants A124D, R153G, A235D, W365A, W365G, W365S, and A366G were expressed well as soluble proteins with a molecular weight similar to that of the wild-type enzyme of 56 kDa. Quite interestingly as obviously seen in the SDS-PAGE (FIG. 4), A366G (lane 2), W365S (lane 5), W365G (lane 6), W365A (lane 7), and R153G (lane 8) mutants had significantly improved expression level of soluble recombinant proteins in the cell lysates compared to the wild-type enzyme (lane 1) as well as A235D (lane 3) and A124D (lane 4) mutants. It was unclear how a single site mutation close to the substrate binding pocket can improve the expression level of the soluble protein in the *Escherichia coli* expression system. Repeated expression in duplicates or triplicates and more detailed quantitation showed that compared to wild-type Psp2,6ST(15-501)-His$_6$ whose expression level fell in a range of 18-40 mg per liter, the A366G mutant was able to be expressed and purified by nickel-nitrilotriacetic acid (Ni$^{2+}$-NTA) column chromatography in a range of 72-110 mg per liter of *Escherichia coli* culture—reaching over a six-fold increase.

Example 3. Activity Comparison of Psp26ST(15-501)-His$_6$ and Mutants

Procedure for Sialyltransferase Activity Assays for Psp26ST(15-501)-His$_6$ and Mutants.

When LacβMU was used as an acceptor, the assay was performed in duplicate in 10 μL of Tris-HCl buffer (100 mM, pH 8.0) containing CMP-Neu5Ac (1 mM), LacβMU (1 mM), MgCl$_2$ (20 mM), wild-type Psp2,6ST(15-501)-His$_6$ or its mutant (0.3 μM). When an α-GalNAc-terminated acceptor was used, the assay was performed in duplicate in 10 μL of Tris-HCl buffer (100 mM, pH 8.0 for GalNAcαSer/Thr) or NaOAc-HOAc (100 mM, pH 5.0 for GalNAcα2AA) containing CMP-Neu5Ac (1.5 mM), the acceptor (1 mM), MgCl$_2$ (20 mM), wild-type Psp2,6ST(15-501)-His$_6$ or its mutant (3.0 μM). Reactions were allowed to proceed at 20° C. for 20 min and stopped by adding 10 μL of cold ethanol. The analysis of sialylated product conversion was performed using the HPLC system as described above for sialyltransferase activity assay. The 4-methylumbelliferone (MU)-labeled fluorescent acceptor and the product formed were detected with excitation at 325 nm and emission at 372 nm. The 2-aminobenzoic acid (2AA)-labeled fluorescent acceptors and the products formed were detected with excitation at 315 nm and emission at 400 nm. The 9-fluorenylmethylcarbamate (Fmoc)-labeled fluorescent acceptors and the products formed were detected with excitation at 262 nm and emission at 313 nm.

Results.

Activity assays using LacβMU, GalNAcα2AA, GalNAcαSer, or GalNAcαThr as an acceptor for Psp2,6ST(15-501)-His$_6$ and mutants (FIG. 5) showed that the activities of W365 mutants, including W365A, W365G, and W365S, decreased drastically in sialylating LacβMU (1-5% activity of the wild-type enzyme) and GalNAcαSer (9-16% activity of the wild-type enzyme) and the effect was more severe for LacβMU. The activities of W365 mutants also decreased in sialylating GalNAcα2AA (39-62% activity of the wild-type enzyme) and GalNAcαThr (65-82% activity of the wild-type enzyme), but to a lesser extent. These results indicated that the acceptor stabilizing effect by Trp365 van der Waals stacking interactions is more significant when LacβMU or GalNAcαSer was used as the acceptor instead of GalNAcα2AA or GalNAcαThr (see also, Ni and Chen, et al. *Biochemistry* 2007, 46, 6288-6298). Changing the bulkier tryptophan residue to a smaller alanine, glycine, or serine residue did not appear to provide a benefit in accommodating α-linked N-acetyl galactosides as acceptor substrates for Psp2,6ST(15-501)-His$_6$. Mutating R153, a residue that is conserved among GT80 sialyltransferases characterized so far, to a glycine residue knocked out the sialylation activity completely. The corresponding R63 in PmST1 was shown to form ion pairs with the sialyl carboxylic acid group which explains the importance of the negative charge in the residue. See, Ni, 2007, supra.

Advantageously, the A366G mutant of Psp2,6ST(15-501)-His$_6$ exhibited improved sialyltransferase activity when α-linked N-acetyl galactosaminides, especially GalNAcα2AA or GalNAcαThr, were used as the acceptor. These results indicate that a smaller glycine residue may provide a bigger acceptor binding pocket to accommodate α-linked N-acetyl galactosaminides.

Figure 5A:
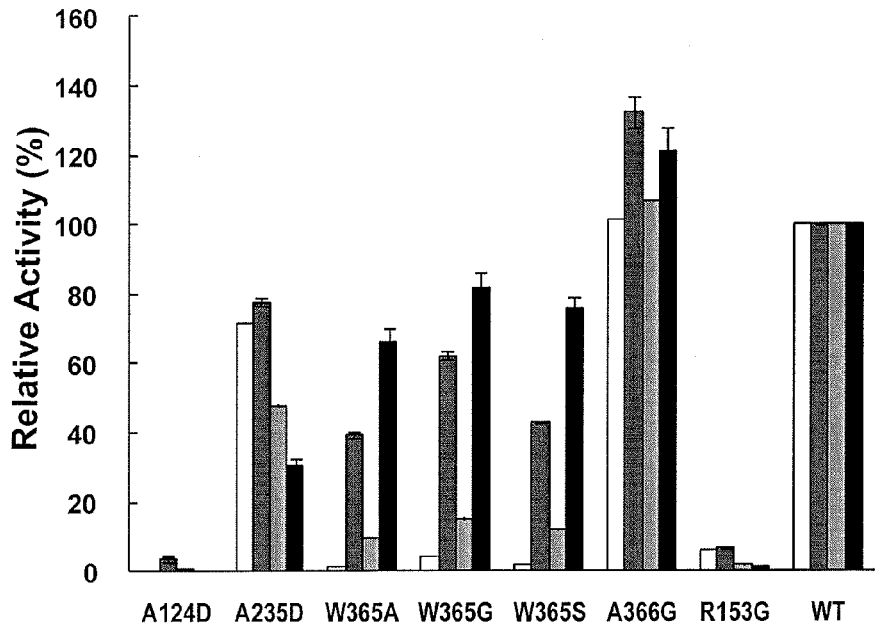
FIG. 5A shows the relative sialyltransferase activities of Psp2,6ST(15-501)-His$_6$ and its mutants, when different acceptors were used and the observed activities for the wild-type enzyme were assigned as 100%. LacβMU (white columns), GalNAcα2AA (dark grey columns), GalNAcαSer (light grey columns) and GalNAcαThr (black columns).

Similar to that observed previously for PmST1 A35D and A35H mutants, the corresponding Psp2,6ST(15-501)-His$_6$ A124D mutant lost sialylation activity. In comparison, the Psp2,6ST(15-501)-His$_6$ A235D mutant did have a decreased donor hydrolysis activity (Table 2) while maintaining most of the sialylation activity (FIG. 5). The CMP-Neu5Ac hydrolysis efficiency catalyzed by Psp2,6ST(15-501)-His$_6$ was 17 mM$^{-1}$ min$^{-1}$, which was about 14-fold more efficient than its sialyltransferase activity when GalNAcα2AA was used as an acceptor ($k_{cat}/K_m$=1.2 mM$^{-1}$ min$^{-1}$), although it was 13-fold lower than the sialyltransferase activity when LacβMU was used as acceptor ($k_{cat}/K_m$=2.2×10$^2$ mM$^{-1}$ min$^{-1}$). This can explain the lower yield of sialylating GalNAcα2AA by Psp2,6ST(15-501)-His$_6$. In comparison, the CMP-Neu5Ac hydrolysis efficiency catalyzed by a closely related *Photobacterium damselae* α2-6-sialyltransferase His$_6$-Pd2,6ST(16-497) was 12 mM$^{-1}$ min$^{-1}$ (Table 2) which was very similar to that of Psp2,6ST(15-501)-His$_6$ (see, e.g., Yu, *Angew. Chem. Int. Ed.* 2006, supra; Sun, 2008, supra). For Psp2,6ST(15-501)-His$_6$ A235D mutant, the efficiency for donor hydrolysis was 6.6 mM$^{-1}$ min$^{-1}$. However, this decreased donor hydrolysis did not lead to the overall improvement of the sialylation efficiency of the enzyme.

TABLE 2

Apparent kinetic parameters for the CMP-Neu5Ac hydrolysis activities of Psp2,6ST(15-501)-His$_6$ and A235D mutant.

| Enzyme | $K_m$ (mM) | $k_{cat}$ (min$^{-1}$) | $k_{cat}/K_m$ (mM$^{-1}$ min$^{-1}$) |
|---|---|---|---|
| His$_6$-Pd2,6ST (16-497) | (1.8 ± 0.4) × 10 | (2.2 ± 0.2) × 10$^2$ | 1.2 × 10 |
| Psp2,6ST (15-501)-His$_6$ | (1.7 ± 0.4) × 10 | (2.9 ± 0.3) × 10$^2$ | 1.7 × 10 |
| Psp2,6ST (15-501)-His$_6$ A235D mutant | (3.8 ± 0.5) × 10 | (2.5 ± 0.2) × 10$^2$ | 6.6 |

Example 4. Kinetic Study of Psp26ST(15-501)-His$_6$ A366G Mutant

Procedure.

Reactions were carried out in duplicate at 20° C. for 20 minutes in a total volume of 10 μL in a proper buffer at the optimal pH according to the pH profile of the wild-type enzyme (see, Ding, 2011, supra). When LacβMU was used as an acceptor, the conditions were: Tris-HCl buffer (200 mM, pH 8.0), enzyme (0.3 μM), varied concentrations of LacβMU (0.1, 0.25, 0.4, 1.0, 2.0, 4.0, and 6.0 mM) with a fixed concentration of CMP-Neu5Ac (1.0 mM) or varied concentrations of CMP-Neu5Ac (0.1, 0.25, 0.4, 1.0, 2.0, 4.0, and 6.0 mM) with a fixed concentration of LacβMU (1.0 mM). When GalNAcα2AA was used as an acceptor, the conditions were: NaOAc-HOAc buffer (200 mM, pH 5.0), enzyme (6 μM), varied concentrations of GalNAcα2AA (0.5, 0.8, 1.0, 2.0, 4.0, 8.0, and 10.0 mM) and a fixed concentration of CMP-Neu5Ac (4.0 mM) or varied concentrations of CMP-Neu5Ac (0.5, 1.0, 2.0, 4.0, 5.0, 8.0, and 10.0 mM) with a fixed concentration of GalNAcα2AA (1.0 mM). When GalNAcαSer was used as an acceptor, the conditions were: Tris-HCl buffer (200 mM, pH 8.0), enzyme (0.6 μM), varied concentrations of GalNAcαSer (0.1, 0.25, 0.5, 1.0, 2.0, 4.0, 8.0, and 10.0 mM) and a fixed concentration of CMP-Neu5Ac (2.0 mM). When GalNAcαThr was used as an acceptor, the conditions were: Tris-HCl buffer (200 mM, pH 8.0), enzyme (3.0 µM), varied concentrations of GalNAcαThr (0.5, 1.0, 2.0, 4.0, 10.0, 20.0, 40.0, 60.0 mM) and a fixed concentration of CMP-Neu5Ac (4.0 mM). Results analysis was performed using the HPLC system as described above for sialyltransferase activity assays. Apparent kinetic parameters were obtained by fitting the experimental data (the average values of duplicate assay results) into the Michaelis-Menten equation using Grafit 5.0.

Results.

Figure 5B:
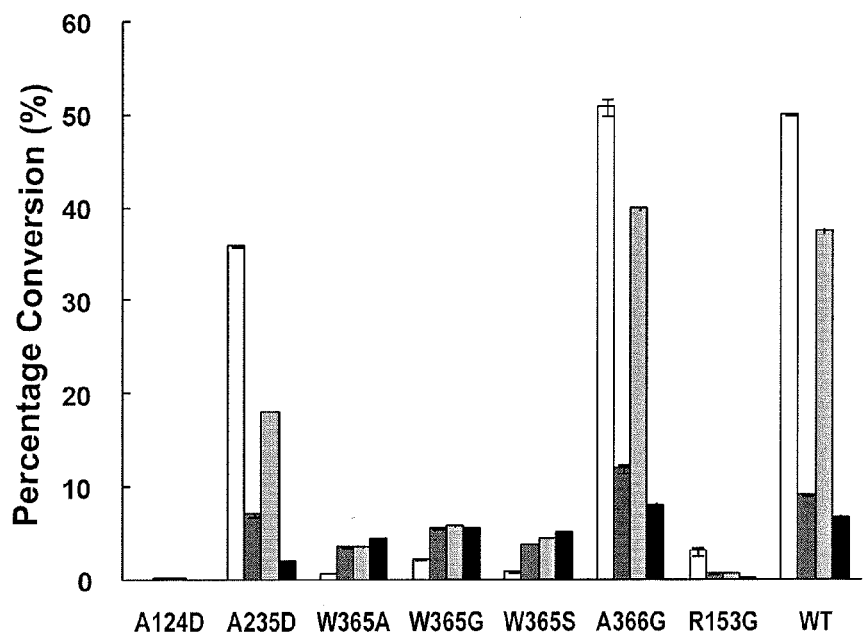
FIG. 5B shows the percentage conversions of sialylation reactions catalyzed by Psp2,6ST(15-501)-His$_6$ and its mutants, when different acceptors were used. LacβMU (white columns), GalNAcα2AA (dark grey columns), GalNAcαSer (light grey columns) and GalNAcαThr (black columns).
Figure 6:
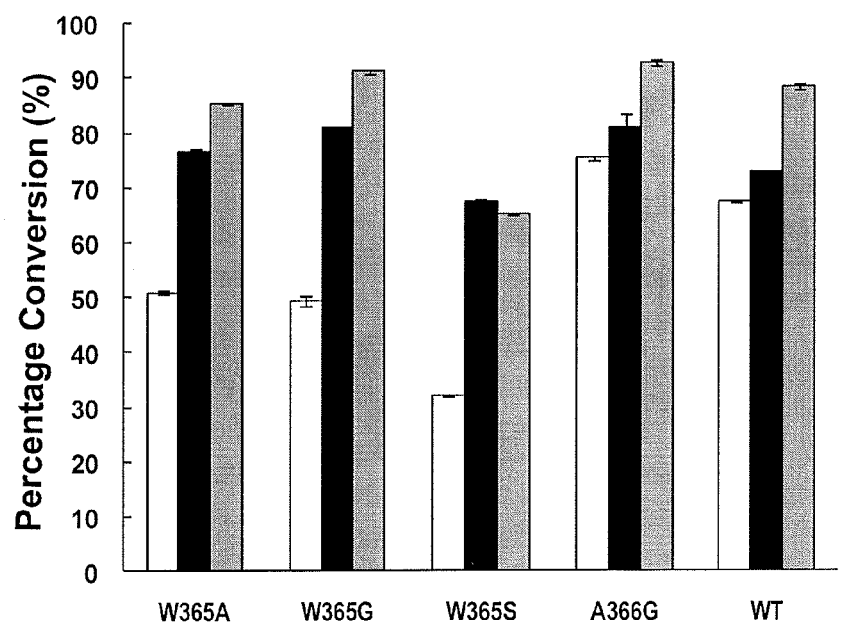
FIG. 6 shows yields from one-pot two-enzyme (OP2E) reactions containing Neisseria meningitidis CMP-sialic acid synthetase and Psp2,6ST(15-501)-His$_6$ or its mutants. White bars: GalNAcαSer was used as an acceptor with 1 equivalent of Neu5Ac and 1.5 equivalents of CTP. Grey bars: GalNAcαSer was used as an acceptor with 2.5 equivalents of Neu5Ac and 5.0 equivalents of CTP. Black bars: GalNAcαThr was used as an acceptor with 2.5 equivalents of Neu5Ac and 5.0 equivalents of CTP.

Among the mutants obtained, the A366G mutant which has an enhanced expression level and improved sialylation activities was characterized further. Kinetics studies showed that its catalytic efficiencies ($k_{cat}/K_m$) were 4.4, 29, and 5.7 $mM^{-1}$ $min^{-1}$, respectively, when GalNAcα2AA, GalNAcαSer, and GalNAcαThr were used as the acceptor substrates, which were 1.3, 1.2 and 2.1-fold higher than those of the wild-type enzyme (Table 3). For acceptor GalNAcα2AA, the decreased $K_m$ value contributed to the improved catalytic efficiency of the mutant. For acceptors GalNAcαSer and GalNAcαThr, higher $k_{cat}$ values contributed to the enhanced catalytic efficiencies of the mutant. For acceptor LacβMU, the $k_{cat}$ and the $K_m$ value of the mutant remained almost the same as the wild-type enzyme, leading to similar $k_{cat}/K_m$ values for the mutant and the wild-type enzyme. Overall, compared to the wild-type Psp26ST(15-501)-His$_6$, the A366G mutant has improved catalytic efficiency towards α-linked N-acetylgalactosaminides without changing its efficiency in sialylating β-linked galactosides.

mutants. As shown in FIG. 6, the application of the one-pot multienzyme (OPME) approach effectively improved the yields of STn formation compared to the reactions catalyzed by Psp26ST(15-501)-His$_6$ or its mutants alone (FIG. 5B). For example, using 1 equivalent of Neu5Ac and 1.5 equivalents of CTP in the one-pot two-enzyme (OP2E) reaction (white bars in FIG. 6) improved the GalNAcαSer α2-6-sialylation reaction yields from less than 6% (1 equivalent CMP-Neu5Ac was used) (FIG. 5B) to 32-51% for W365A, W365G, W365S mutants. Similarly, the OP2E reaction improved the GalNAcαSer α2-6-sialylation reaction yields from 40% and 37% to 75% and 67% for A366G mutant and the wild-type enzyme, respectively. Increasing the concentrations of Neu5Ac and CTP to 2.5 and 5.0 equivalents further improved the reaction yields to more than 67% for Psp26ST(15-501)-His$_6$ and its mutants (black bars in FIG. 6). Quite significantly, the yields for synthesizing Neu5Acα2-6GalNAcαThr from GalNAcαThr, a poorer acceptor for Psp26ST(15-501)-His$_6$ and mutants other than A366G, were improved to more than 65% for all enzymes and reached 85%, 91%, 93%, and 88% for W365A, W365G, A366G mutants and the wild-type enzyme, respectively (grey bars in FIG. 6). Therefore, in situ generation of CMP-Neu5Ac, the sugar nucleotide donor for sialyltransferases, was proven an efficient method to enhance the yields for sialylation reactions catalyzed not only by the wild-type enzymes but also sialyltransferase mutants.

The Psp26ST(15-501)-His$_6$ mutant (A366G) described herein exhibited an enhanced expression level and improved activity in catalyzing the formation of Neu5Acα2-6GalNAcαSer/Thr STn antigens was generated and characterized. Protein crystal structure-based site-directed muta-

TABLE 3

Apparent kinetic parameters of Psp26ST(15-501)-His$_6$ and A366G mutant.

| Enzyme | Substrate | $K_m$ (mM) | $k_{cat}$ (min$^{-1}$) | $k_{cat}/K_m$ (mM$^{-1}$ min$^{-1}$) |
|---|---|---|---|---|
| Psp26ST(15-501)-His$_6{}^a$ | CMP-Neu5Ac | $(6.2 \pm 0.4) \times 10^{-1}$ | $(1.4 \pm 0.1) \times 10^2$ | $2.2 \times 10^2$ |
|  | LacβMU | $(3.6 \pm 0.7) \times 10^{-1}$ | $(1.0 \pm 0.1) \times 10^2$ | $2.9 \times 10^2$ |
|  | CMP-Neu5Ac | $3.9 \pm 0.4$ | $4.8 \pm 0.2$ | 1.2 |
|  | GalNAcα2AA | $9.5 \pm 2.7$ | $(3.1 \pm 0.5) \times 10$ | 3.3 |
|  | GalNAcαOSer | $1.4 \pm 0.1$ | $(3.4 \pm 0.3) \times 10$ | $2.4 \times 10$ |
|  | GalNAcαOThr | $5.9 \pm 1.6$ | $(1.6 \pm 0.1) \times 10$ | 2.7 |
| Psp26ST(15-501)-His$_6$ | CMP-Neu5Ac | $(6.3 \pm 0.5) \times 10^{-1}$ | $(1.3 \pm 0.1) \times 10^2$ | $2.1 \times 10^2$ |
|  | LacβMU | $(4.1 \pm 0.4) \times 10^{-1}$ | $(1.0 \pm 0.1) \times 10^2$ | $2.4 \times 10^2$ |
| A366G mutant | CMP-Neu5Ac | $3.3 \pm 0.4$ | $5.9 \pm 0.2$ | 1.8 |
|  | GalNAcα2AA | $5.5 \pm 1.0$ | $(2.4 \pm 0.1) \times 10$ | 4.4 |
|  | GalNAcαOSer | $1.7 \pm 0.7$ | $(4.9 \pm 1.2) \times 10$ | $2.9 \times 10$ |
|  | GalNAcαOThr | $7.2 \pm 3.0$ | $(4.2 \pm 0.5) \times 10$ | 5.8 |

$^a$The kinetic parameters for the wild-type enzyme are taken from Ding, 2011, supra.

Example 5. Efficiency of a One-Pot Two-Enzyme System for Synthesizing STn Antigens Using Psp26ST(15-501)-His$_6$ and Mutants Psp26ST(15-501)-His$_6$ mutants A366G, W365G, W365A, and W365S which showed high expression levels and good or reasonable α2-6-sialyltransferase activities for sialylating α-linked N-acetylgalactosaminides were used with *Neisseria meningitidis* CMP-sialic acid synthetase (NmCSS) in a one-pot two-enzyme system for synthesizing STn antigens from Tn-antigens GalNAcαSer (white and black bars in FIG. 6) and GalNAcαThr (Grey bars in FIG. 6) in the presence of Neu5Ac and CTP. In this system, CTP and Neu5Ac were used by NmCSS for the formation of CMP-Neu5Ac in situ (see also, Yu and Chen, et al. *Bioorg. Med. Chem.* 2004, 12, 6427-6435). CMP-Neu5Ac was used as the donor substrate for Psp26ST(15-501)-His$_6$ or its genesis was demonstrated as a practical approach to obtain sialyltransferase mutants with improved function. In situ generation of CMP-Neu5Ac by one-pot multienzyme (OPME) system was also confirmed to be an efficient approach for high-yield enzymatic and chemoenzymatic synthesis of sialosides.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

INFORMAL SEQUENCE LISTING:

Psp26ST(15-501) A366G (DNA)

SEQ ID NO: 1

ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGTTTGATTTTAATGGCGTGAGCA
ATAAAGGCGAAAAATATATTACCAAAGTGACCCTGATGTGTGGCACCGAGCCTGGAAGTTTA
TGTTGATCATGCAAGCCTGCCGACCCTGCAGCAGCTGATGGATATTATTAAAAGCGAAGAAGAA
AATCCGACCGCACAGCGTTATATTGCATGGGGTCGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGCAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGCAGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTTGGGGTGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATACCCTGATTATGCAGAATT
ATCCGAGCATGGTTGATATTCCGAGCAAAATTTCCTTTGAAGTGCTGATGATGACCGATATGCT
GCCGGATGCAGTTGCAGGTATTGCAAGCAGCCTGTATTTTACCATTCCGGCAGAAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTGGGCACTCGAGCA
CCACCACCACCACCACTGAGATCCGGCTGCTAACAAAGCCCGAAAG

Psp26ST(15-501) A366G (PROTEIN)

SEQ ID NO: 2

| | | | | | |
|---|---|---|---|---|---|
| | 15 | CNNSEE NTQSIIKNDI | NKTIIDEEYV | NLEPINQSNI | 50 |
| 51 | SFTKHSWVQT | CGTQQLLTEQ | NKESISLSVV | APRLDDDEKY | CFDFNGVSNK | 100 |
| 101 | GEKYITKVTL | NVVAPSLEVY | VDHASLPTLQ | QLMDIIKSEE | ENPTAQRYIA | 150 |
| 151 | WGRIVPTDEQ | MKELNITSFA | LINNHTPADL | VQEIVKQAQT | KHRLNVKLSS | 200 |
| 201 | NTAHSFDNLV | PILKELNSFN | NVTVTNIDLY | DDGSAEYVNL | YNWRDTLNKT | 250 |
| 251 | DNLKIGKDYL | EDVINGINED | TSNTGTSSVY | NWQKLYPANY | HFLRKDYLTL | 300 |
| 301 | EPSLHELRDY | IGDSLKQMQW | DGFKKFNSKQ | QELFLSIVNF | DKQKLQNEYN | 350 |
| 351 | SSNLPNFVFT | GTTVWGGNHE | REYYAKQQIN | VINNAINESS | PHYLGNSYDL | 400 |
| 401 | FFKGHPGGGI | INTLIMQNYP | SMVDIPSKIS | FEVLMMTDML | PDAVAGIASS | 450 |
| 451 | LYFTIPAEKI | KFIVFTSTET | ITDRETALRS | PLVQVMIKLG | IVKEENVLFW | 500 |
| 501 | A | | | | |

Psp26ST(15-501) W365G (DNA)

SEQ ID NO: 3

ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGCTTTGATTTTAATGGCGTGAGCA
ATAAAGGCGAAAAATATATTACCAAAGTGACCCTGATGTTGTGGCACCGAGCCTGGAAGTTTA
TGTTGATCATGCAAGCCTGCCGACCCTGCAGCAGCTGATGGATATTATTAAAAGCGAAGAAGAA
AATCCGACCGCACAGCGTTATATTGCATGGGGTCGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGCAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGCAGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTGGCGCAGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATACCCTGATTATGCAGAATT
ATCCGAGCATGGTTGATATTCCGAGCAAAATTTCCTTTGAAGTGCTGATGATGACCGATATGCT
GCCGGATGCAGTTGCAGGTATTGCAAGCAGCCTGTATTTTACCATTCCGGCAGAAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTGGGCACTCGAGCA
CCACCACCACCACCACTGAGATCCGGCTGCTAACAAAGCCCGAAAG

INFORMAL SEQUENCE LISTING:

Psp26ST(15-501) W365G (PROTEIN)  
SEQ ID NO: 4

```
 15  CNNSEE NTQSIIKNDI NKTIIDEEYV NLEPINQSNI   50
 51  SFTKHSWVQT CGTQQLLTEQ NKESISLSVV APRLDDDEKY CFDFNGVSNK  100
101  GEKYITKVTL NVVAPSLEVY VDHASLPTLQ QLMDIIKSEE ENPTAQRYIA  150
151  WGRIVPTDEQ MKELNITSFA LINNHTPADL VQEIVKQAQT KHRLNVKLSS  200
201  NTAHSFDNLV PILKELNSFN NVTVTNIDLY DDGSAEYVNL YNWRDTLNKT  250
251  DNLKIGKDYL EDVINGINED TSNTGTSSVY NWQKLYPANY HFLRKDYLTL  300
301  EPSLHELRDY IGDSLKQMQW DGFKKFNSKQ QELFLSIVNF DKQKLQNEYN  350
351  SSNLPNFVFT GTTVGAGNHE REYYAKQQIN VINNAINESS PHYLGNSYDL  400
401  FFKGHPGGGI INTLIMQNYP SMVDIPSKIS FEVLMMTDML PDAVAGIASS  450
451  LYFTIPAEKI KFIVFTSTET ITDRETALRS PLVQVMIKLG IVKEENVLFW  500
501  A
```

Psp26ST(15-501) W365A (DNA)  
SEQ ID NO: 5

```
ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGCTTTGATTTTAATGGCGTGAGCA
ATAAAGGCGAAAATATATTACCAAAGTGACCCTGAATGTTGTGGCACCGAGCCTGGAAGTTTA
TGTTGATCATGCAAGCCTGCCGACCCTGCAGCAGCTGATGGATATTATTAAAAGCGAAGAAGAA
AATCCGACCGCACAGCGTTATATTGCATGGGGTCGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGCAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGCAGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTGCCGGCAGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATCCCTGATTATGCAGAATT
ATCCGAGCATGGTTGATATTCCGAGCAAAATTTCCTTTGAAGTGCTGATGATGACCGATATGCT
GCCGGATGCAGTTGCAGGTATTGCAAGCAGCCTGTATTTTACCATTCCGGCAGAAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTTGGGCACTCGAGCA
CCACCACCACCACCACTGAGATCCGGCTGCTAACAAAGCCCGAAAG
```

Psp26ST(15-501) W365A (PROTEIN)  
SEQ ID NO: 6

```
 15  CNNSEE NTQSIIKNDI NKTIIDEEYV NLEPINQSNI   50
 51  SFTKHSWVQT CGTQQLLTEQ NKESISLSVV APRLDDDEKY CFDFNGVSNK  100
101  GEKYITKVTL NVVAPSLEVY VDHASLPTLQ QLMDIIKSEE ENPTAQRYIA  150
151  WGRIVPTDEQ MKELNITSFA LINNHTPADL VQEIVKQAQT KHRLNVKLSS  200
201  NTAHSFDNLV PILKELNSFN NVTVTNIDLY DDGSAEYVNL YNWRDTLNKT  250
251  DNLKIGKDYL EDVINGINED TSNTGTSSVY NWQKLYPANY HFLRKDYLTL  300
301  EPSLHELRDY IGDSLKQMQW DGFKKFNSKQ QELFLSIVNF DKQKLQNEYN  350
351  SSNLPNFVFT GTTVAAGNHE REYYAKQQIN VINNAINESS PHYLGNSYDL  400
401  FFKGHPGGGI INTLIMQNYP SMVDIPSKIS FEVLMMTDML PDAVAGIASS  450
451  LYFTIPAEKI KFIVFTSTET ITDRETALRS PLVQVMIKLG IVKEENVLFW  500
501  A
```

INFORMAL SEQUENCE LISTING:

Psp26ST(15-501) W365S (DNA)

SEQ ID NO: 7

```
ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGCTTTGATTTTAATGGCGTGAGCA
ATAAAGGCGAAAAATATATTACCAAAGTGACCCTGAATGTTGTGGCACCGAGCCTGGAAGTTTA
TGTTGATCATCAAGCCTGCCGACCCTGCAGCAGCTGATGGATATTATTAAAGCGGAAGAAGAA
AATCCGACCGCACAGCGTTATATTGCATGGGGTCGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGCAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGCAGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTAGCGCAGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATACCCTGATTATGCAGAATT
ATCCGAGCATGGTTGATATTCCGAGCAAATTTCCTTTGAAGTGCTGATGATGACCGATATGCT
GCCGGATGCAGTTGCAGGTATTGCAAGCAGCCTGTATTTTACCATTCCGGCAGAAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTGGGCACTCGAGCA
CCACCACCACCACCACTGAGATCCGGCTGCTAACAAAGCCCGAAAG
```

Psp26ST(15-501) W365S (PROTEIN)

SEQ ID NO: 8

```
         15 CNNSEE NTQSIIKNDI NKTIIDEEYV NLEPINQSNI     50

51  SFTKHSWVQT CGTQQLLTEQ NKESISLSVV APRLDDDEKY CFDFNGVSNK    100

101  GEKYITKVTL NVVAPSLEVY VDHASLPTLQ QLMDIIKSEE ENPTAQRYIA    150

151  WGRIVPTDEQ MKELNITSFA LINNHTPADL VQEIVKQAQT KHRLNVKLSS    200

201  NTAHSFDNLV PILKELNSFN NVTVTNIDLY DDGSAEYVNL YNWRDTLNKT    250

251  DNLKIGKDYL EDVINGINED TSNTGTSSVY NWQKLYPANY HFLRKDYLTL    300

301  EPSLHELRDY IGDSLKQMQW DGFKKFNSKQ QELFLSIVNF DKQKLQNEYN    350

351  SSNLPNFVFT GTTVSAGNHE REYYAKQQIN VINNAINESS PHYLGNSYDL    400

401  FFKGHPGGGI INTLIMQNYP SMVDIPSKIS FEVLMMTDML PDAVAGIASS    450

451  LYFTIPAEKI KFIVFTSTET ITDRETALRS PLVQVMIKLG IVKEENVLFW    500

501  A
```

Psp26ST(15-501) R153G (DNA)

SEQ ID NO: 9

```
ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGCTTTGATTTTAATGGCGTGAGCA
ATAAAGGCGAAAAATATATTACCAAAGTGACCCTGAATGTTGTGGCACCGAGCCTGGAAGTTTA
TGTTGATCATCAAGCCTGCCGACCCTGCAGCAGCTGATGGATATTATTAAAGCGGAAGAAGAA
AATCCGACCGCACAGCGTTATATTGCATGGGGTGGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGCAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGCAGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTGGGCAGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATACCCTGATTATGCAGAATT
ATCCGAGCATGGTTGATATTCCGAGCAAATTTCCTTTGAAGTGCTGATGATGACCGATATGCT
```

```
GCCGGATGCAGTTGCAGGTATTGCAAGCAGCCTGTATTTTACCATTCCGGCAGAAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTGGGCACTCGAGCA
CCACCACCACCACCACTGAGATCCGGCTGCTAACAAAGCCCGAAAG
```

Psp26ST(15-501) R153G (PROTEIN)

SEQ ID NO: 10

```
         15  CNNSEE NTQSIIKNDI NKTIIDEEYV NLEPINQSNI       50

51  SFTKHSWVQT CGTQQLLTEQ NKESISLSVV APRLDDDEKY CFDFNGVSNK    100

101  GEKYITKVTL NVVAPSLEVY VDHASLPTLQ QLMDIIKSEE ENPTAQRYIA    150

151  WGGIVPTDEQ MKELNITSFA LINNHTPADL VQEIVKQAQT KHRLNVKLSS    200

201  NTAHSFDNLV PILKELNSFN NVTVTNIDLY DDGSAEYVNL YNWRDTLNKT    250

251  DNLKIGKDYL EDVINGINED TSNTGTSSVY NWQKLYPANY HFLRKDYLTL    300

301  EPSLHELRDY IGDSLKQMQW DGFKKFNSKQ QELFLSIVNF DKQKLQNEYN    350

351  SSNLPNFVFT GTTVWAGNHE REYYAKQQIN VINNAINESS PHYLGNSYDL    400

401  FFKGHPGGGI INTLIMQNYP SMVDIPSKIS FEVLMMTDML PDAVAGIASS    450

451  LYFTIPAEKI KFIVFTSTET ITDRETALRS PLVQVMIKLG IVKEENVLFW    500

501  A
```

Psp26ST(15-501) A124D (DNA)

SEQ ID NO: 11

```
ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGCTTTGATTTTAATGGCGTGAGCA
ATAAAGGCGAAAAATATATTACCAAAGTGACCCTGAATGTTGTGGCACCGAGCCTGGAAGTTTA
TGTTGATCATGATAGCCTGCCGACCCTGCAGCAGCTGATGGATATTATTAAAAGCGAAGAAGAA
AATCCGACCGCACAGCGTTATATTGCATGGGGTCGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGGAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGCAGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTTGGGCAGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATACCCTGATTATGCAGAATT
ATCCGAGCATGGTTGATATTCCGAGCAAAATTTCCTTTGAAGTGCTGATGATGACCGATATGCT
GCCGGATGCAGTTGCAGGTATTGCAAGCAGCCTGTATTTTACCATTCCGGCAGAAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTGGGCACTCGAGCA
CCACCACCACCACCACTGAGATCCGGCTGCTAACAAAGCCCGAAAG
```

Psp26ST(15-501) A124D (PROTEIN)

SEQ ID NO: 12

```
         15  CNNSEE NTQSIIKNDI NKTIIDEEYV NLEPINQSNI       50

51  SFTKHSWVQT CGTQQLLTEQ NKESISLSVV APRLDDDEKY CFDFNGVSNK    100

101  GEKYITKVTL NVVAPSLEVY VDHDSLPTLQ QLMDIIKSEE ENPTAQRYIA    150

151  WGRIVPTDEQ MKELNITSFA LINNHTPADL VQEIVKQAQT KHRLNVKLSS    200

201  NTAHSFDNLV PILKELNSFN NVTVTNIDLY DDGSAEYVNL YNWRDTLNKT    250

251  DNLKIGKDYL EDVINGINED TSNTGTSSVY NWQKLYPANY HFLRKDYLTL    300

301  EPSLHELRDY IGDSLKQMQW DGFKKFNSKQ QELFLSIVNF DKQKLQNEYN    350

351  SSNLPNFVFT GTTVWAGNHE REYYAKQQIN VINNAINESS PHYLGNSYDL    400
```

| | | |
|---|---|---|
| 401 | FFKGHPGGGI INTLIMQNYP SMVDIPSKIS FEVLMMTDML PDAVAGIASS | 450 |
| 451 | LYFTIPAEKI KFIVFTSTET ITDRETALRS PLVQVMIKLG IVKEENVLFW | 500 |
| 501 | A | |

Psp26ST(15-501) A235D (DNA)
SEQ ID NO: 13

ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGGTTTGATTTTAATGGCGTGAGCA
ATAAAGGCGAAAAATATATTACCAAAGTGACCCTGAATGTTGTGGCACCGAGCCTGGAAGTTTA
TGTTGATCATGCAAGCCTGCCGACCCTGCAGCAGCTGATGGATATTATTAAAAGCGAAGAAGAA
AATCCGACCGCACAGCGTTATATTGCATGGGGTCGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGCAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGATGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTTGGGCAGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATACCCTGATTATGCAGAATT
ATCCGAGCATGGTTGATATTCCGAGCAAAATTTCCTTTGAAGTGCTGATGATGACCGATATGCT
GCCGGATGCAGTTCAGGTATTGCAAGCAGCCTGTATTTTACCATTCCGGCAGAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTTGGGCACTCGAGCA
CCACCACCACCACCACTGAGATCCGGCTGCTAACAAAGCCCGAAAG

Psp26ST(15-501) A235D (PROTEIN)
SEQ ID NO: 14

| | | |
|---|---|---|
| | 15 CNNSEE NTQSIIKNDI NKTIIDEEYV NLEPINQSNI | 50 |
| 51 | SFTKHSWVQT CGTQQLLTEQ NKESISLSVV APRLDDDEKY CFDFNGVSNK | 100 |
| 101 | GEKYITKVTL NVVAPSLEVY VDHASLPTLQ QLMDIIKSEE ENPTAQRYIA | 150 |
| 151 | WGRIVPTDEQ MKELNITSFA LINNHTPADL VQEIVKQAQT KHRLNVKLSS | 200 |
| 201 | NTAHSFDNLV PILKELNSFN NVTVTNIDLY DDGSDEYVNL YNWRDTLNKT | 250 |
| 251 | DNLKIGKDYL EDVINGINED TSNTGTSSVY NWQKLYPANY HFLRKDYLTL | 300 |
| 301 | EPSLHELRDY IGDSLKQMQW DGFKKFNSKQ QELFLSIVNF DKQKLQNEYN | 350 |
| 351 | SSNLPNFVFT GTTVWAGNHE REYYAKQQIN VINNAINESS PHYLGNSYDL | 400 |
| 401 | FFKGHPGGGI INTLIMQNYP SMVDIPSKIS FEVLMMTDML PDAVAGIASS | 450 |
| 451 | LYFTIPAEKI KFIVFTSTET ITDRETALRS PLVQVMIKLG IVKEENVLFW | 500 |
| 501 | A | |

Synthetic primer A366G (DNA)
SEQ ID NO: 15

1    GGCACCACCG TTTGGGGTGG TAATCATGAA CG    32

Synthetic primer W365G (DNA)
SEQ ID NO: 16

1    TTACCGGCAC CACCGTTGGC GCAGGTAATC ATGAACG    37

Synthetic primer W365A (DNA)
SEQ ID NO: 17

1    TTACCGGCAC CACCGTTGCG GCAGGTAATC ATGAACG    37

Synthetic primer W365S (DNA)
SEQ ID NO: 18

1    TTACCGGCAC CACCGTTAGC GCAGGTAATC ATGAACG    37

Synthetic primer R153G (DNA)
SEQ ID NO: 19

1    CGTTATATTG CATGGGGTGG TATTGTTCCG ACCGATGAG    39

INFORMAL SEQUENCE LISTING:

Synthetic primer A124D (DNA)

SEQ ID NO: 20

```
  1   GAAGTTTATG TTGATCATGA TAGCCTGCCG ACCCTGCAG        39
```

Synthetic primer A235D (DNA)

SEQ ID NO: 21

```
  1   TCTGTATGAC GATGGCAGCG ATGAGTACGT GAATCTGTAT AAT    43
```

Psp26ST(15-501) WILD TYPE (DNA)

SEQ ID NO: 22

```
ATGTGTAATAATAGCGAAGAAAATACCCAGAGCATCATTAAAAATGATATCAACAAAACCATCA
TTGATGAAGAATACGTGAACCTGGAACCGATTAATCAGAGCAATATTAGCTTTACCAAACATAG
CTGGGTTCAGACCTGTGGCACCCAGCAACTGCTGACCGAACAGAATAAAGAAAGCATTAGCCTG
AGCGTTGTTGCACCGCGTCTGGATGATGATGAGAAATATTGCTTTGATTTTAATGGCGTGAGCA
ATAAAGGCGAAAAATATATTACCAAAGTGACCCTGAATGTTGTGGCACCGAGCCTGGAAGTTTA
TGTTGATCATGCAAGCCTGCCGACCCTGCAGCAGCTGATGGATATTATTAAAAGCGAAGAAGAA
AATCCGACCGCACAGCGTTATATTGCATGGGGTCGTATTGTTCCGACCGATGAGCAGATGAAAG
AACTGAATATTACCAGCTTTGCCCTGATTAATAATCATACACCGGCAGATCTGGTTCAGGAAAT
TGTTAAACAGGCCCAGACCAAACATCGTCTGAATGTTAAACTGAGCAGCAATACCGCACATAGC
TTTGATAATCTGGTGCCGATTCTGAAAGAGCTGAATTCCTTTAATAATGTGACCGTGACCAATA
TTGATCTGTATGACGATGGCAGCGCAGAGTACGTGAATCTGTATAATTGGCGTGATACCCTGAA
TAAAACCGATAATCTGAAAATTGGCAAAGATTACCTGGAAGATGTGATTAATGGCATTAATGAA
GATACCAGCAATACCGGCACCAGCAGCGTTTATAATTGGCAGAAACTGTATCCGGCAAATTATC
ATTTTCTGCGTAAAGACTACCTGACCCTGGAACCGAGCCTGCATGAACTGCGTGATTATATTGG
CGATAGCCTGAAACAAATGCAGTGGGATGGCTTTAAAAAATTTAATAGCAAACAGCAGGAACTG
TTTCTGAGCATTGTGAATTTTGATAAACAGAAACTGCAGAATGAATATAATAGCAGCAATCTGC
CGAACTTTGTTTTTACCGGCACCACCGTTTGGGCAGGTAATCATGAACGTGAGTATTATGCCAA
ACAGCAGATTAATGTGATTAATAATGCGATTAATGAAAGCTCTCCGCATTATCTGGGTAATAGC
TATGACCTGTTTTTTAAAGGTCATCCGGGTGGTGGTATTATTAATCCCTGATTATGCAGAATT
ATCCGAGCATGGTTGATATTCCGAGCAAAATTTCCTTTGAAGTGCTGATGATGACCGATATGCT
GCCGGATGCAGTTGCAGGTATTGCAAGCAGCCTGTATTTTACCATTCCGGCAGAAAAAATCAAA
TTTATTGTGTTTACCAGCACCGAAACCATTACCGATCGTGAAACCGCACTGCGTTCTCCGCTGG
TTCAGGTTATGATTAAACTGGGCATTGTGAAGGAGGAAAACGTCCTGTTTTGGGCACTCGAGCA
CCACCACCACCACCACTGAGATCCGGCTGCTAACAAAGCCCGAAAG
```

Psp26ST(15-501) WILD TYPE (PROTEIN)

SEQ ID NO: 23

```
 15   CNNSEE NTQSIIKNDI NKTIIDEEYV NLEPINQSNI       50
 51   SFTKHSWVQT CGTQQLLTEQ NKESISLSVV APRLDDDEKY CFDFNGVSNK  100
101   GEKYITKVTL NVVAPSLEVY VDHASLPTLQ QLMDIIKSEE ENPTAQRYIA  150
151   WGRIVPTDEQ MKELNITSFA LINNHTPADL VQEIVKQAQT KHRLNVKLSS  200
201   NTAHSFDNLV PILKELNSFN NVTVTNIDLY DDGSAEYVNL YNWRDTLNKT  250
251   DNLKIGKDYL EDVINGINED TSNTGTSSVY NWQKLYPANY HFLRKDYLTL  300
301   EPSLHELRDY IGDSLKQMQW DGFKKFNSKQ QELFLSIVNF DKQKLQNEYN  350
351   SSNLPNFVFT GTTVWAGNHE REYYAKQQIN VINNAINESS PHYLGNSYDL  400
401   FFKGHPGGGI INTLIMQNYP SMVDIPSKIS FEVLMMTDML PDAVAGIASS  450
451   LYFTIPAEKI KFIVFTSTET ITDRETALRS PLVQVMIKLG IVKEENVLFW  500
501   A
```

---

What is claimed is:

1. An isolated polypeptide comprising the amino acid sequence set forth in SEQ ID NO: 2, SEQ ID NO: 4, SEQ ID NO: 6, or SEQ ID NO: 8.

2. The polypeptide of claim 1, comprising the amino acid sequence set forth in SEQ ID NO: 2, SEQ ID NO: 4, or SEQ ID NO: 6.

3. The polypeptide of claim 1, comprising the amino acid sequence set forth in SEQ ID NO: 2.

4. The polypeptide of claim 1, further comprising one or more heterologous amino acid sequences located at the N-terminus and/or the C-terminus of the polypeptide.

5. An isolated nucleic acid comprising a polynucleotide sequence encoding the polypeptide of claim 1.

6. The nucleic acid of claim 5, wherein the polynucleotide sequence comprises the polynucleotide sequence set forth in SEQ ID NO: 1, SEQ ID NO: 3, SEQ ID NO: 5, or SEQ ID NO: 7.

7. The nucleic acid of claim 5, wherein the polynucleotide sequence comprises the polynucleotide sequence set forth in SEQ ID NO: 1.

8. An expression cassette comprising the nucleic acid of claim 5 and a promoter, wherein the nucleic acid is operably linked to the promoter.

9. A vector comprising the nucleic acid of claim 5.

10. An isolated host cell comprising the nucleic acid of claim 5.

11. A method of synthesizing a sialylated product, the method comprising;
    forming a reaction mixture comprising:
        an acceptor glycoside,
        a sialic acid donor, and
        the polypeptide of claim 1, and
    incubating the reaction mixture under conditions sufficient to form the sialylated product.

12. The method of claim 11, wherein the polypeptide comprises the amino acid sequence set forth in SEQ ID NO: 2.

13. The method of claim 11, wherein the sialic acid donor is a cytidine-5'-monophosphate sialic acid.

14. The method of claim 11, wherein the sialylated product comprises a sialylated α-linked GalNAc moiety or a sialylated β-linked Gal moiety.

15. The method of claim 14, wherein the sialylated α-linked GalNAc moiety is a Neu5Acα2-6GalNAc moiety.

16. The method of claim 11, wherein the sialylated product is a Siaα2-6GalNAcα1-O-Ser/Thr (sialyl Tn) antigen.

17. The method of claim 16, wherein the acceptor glycoside has a structure according to the formula:

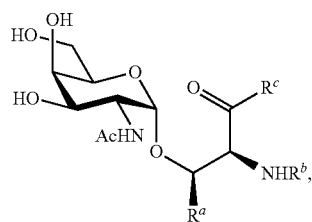

or a salt thereof, wherein:
Ac is acetyl
$R^a$ is selected from the group consisting of H and $CH_3$,
$R^b$ is selected from the group consisting of H, an amino acid residue, an oligopeptide, and a polypeptide, and
$R^c$ is selected from the group consisting of OH, an amino acid residue, an oligopeptide, and a polypeptide.

18. The method of claim 16, wherein the sialyl Tn antigen has a structure according to the formula:

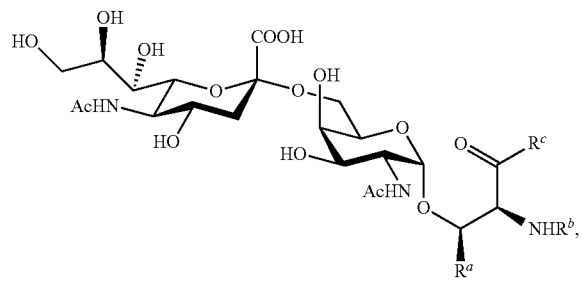

or a salt thereof, wherein:
Ac is acetyl
$R^a$ is selected from the group consisting of H and $CH_3$,
$R^b$ is selected from the group consisting of H, an amino acid residue, an oligopeptide, and a polypeptide, and
$R^c$ is selected from the group consisting of OH, an amino acid residue, an oligopeptide, and a polypeptide.

19. The method of claim 17, wherein $R^b$ and Re are independently a polypeptide.

20. The method of claim 19, wherein $R^b$ and Re are optionally and independently glycosylated.

* * * * *

UNITED STATES PATENT AND TRADEMARK OFFICE
CERTIFICATE OF CORRECTION

PATENT NO. : 9,938,510 B2
APPLICATION NO. : 14/970302
DATED : April 10, 2018
INVENTOR(S) : Xi Chen and Li Ding Page 1 of 1

It is certified that error appears in the above-identified patent and that said Letters Patent is hereby corrected as shown below:

In the Claims

Claim 19, Column 78, Line 44:
Please delete "Re" and insert --$R^c$--.

Claim 20, Column 78, Line 46:
Please delete "Re" and insert --$R^c$--.

Signed and Sealed this
Seventh Day of August, 2018

Andrei Iancu
*Director of the United States Patent and Trademark Office*